(12) United States Patent
Sasamoto

(10) Patent No.: US 8,477,436 B2
(45) Date of Patent: Jul. 2, 2013

(54) OBJECTIVE LENS FOR ENDOSCOPE

(75) Inventor: Tsutomu Sasamoto, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 434 days.

(21) Appl. No.: 12/404,918

(22) Filed: Mar. 16, 2009

(65) Prior Publication Data

US 2009/0237807 A1 Sep. 24, 2009

(30) Foreign Application Priority Data

Mar. 18, 2008 (JP) .................. 2008-069708

(51) Int. Cl.
*G02B 9/04* (2006.01)
*G02B 21/02* (2006.01)
*G02B 23/24* (2006.01)

(52) U.S. Cl.
CPC .............. *G02B 9/04* (2013.01); *G02B 23/2407* (2013.01)
USPC .......................................... 359/793; 359/661

(58) Field of Classification Search
CPC ................................ G02B 9/04; G02B 23/2407
USPC .................... 359/661, 656, 793, 794–795
See application file for complete search history.

(56) References Cited

U.S. PATENT DOCUMENTS

| | | | | |
|---|---|---|---|---|
| 5,087,989 A | * | 2/1992 | Igarashi | 359/692 |
| 5,828,498 A | * | 10/1998 | Sekiya et al. | 359/660 |
| 6,181,481 B1 | * | 1/2001 | Yamamoto et al. | 359/661 |
| 7,486,449 B2 | * | 2/2009 | Miyano | 359/781 |
| 7,961,408 B2 | * | 6/2011 | Lo et al. | 359/753 |

FOREIGN PATENT DOCUMENTS

| | | |
|---|---|---|
| JP | H02-277015 A | 11/1990 |
| JP | H8-122632 | 5/1996 |
| JP | H09-080305 A | 3/1997 |
| JP | H10-020189 | 1/1998 |
| JP | H10-260348 A | 9/1998 |
| JP | 2002-028126 A | 1/2002 |
| JP | 2004-61763 | 2/2004 |
| JP | 2004-145256 A | 5/2004 |
| JP | 2004-354888 | 12/2004 |
| JP | 2007-025499 A | 2/2007 |
| JP | 2008-089658 A | 4/2008 |

OTHER PUBLICATIONS

JP H09-080305 Machine Translation.*

* cited by examiner

*Primary Examiner* — Zachary Wilkes

(74) *Attorney, Agent, or Firm* — Arnold International; Bruce Y. Arnold

(57) ABSTRACT

An objective lens for an endoscope includes, in order from an object side, a front lens group having negative refractive power as a whole, a brightness aperture stop, and a rear lens group having positive refractive power as a whole. The front lens group includes, in order from the object side, a first lens group having negative refractive power and that may include only a single lens; and a second lens group that may include only a single lens, with the second lens group having a lens surface closest to the image side that is of a concave form directed toward the image side, the second lens group having positive refractive power as a whole;

and the following condition (1) is satisfied:

$|f_0/f_1| \leq 1.1$      (1)

where
$f_0$ is the composite focal length of the front lens group, and
$f_1$ is the focal length of the first lens group.

4 Claims, 34 Drawing Sheets

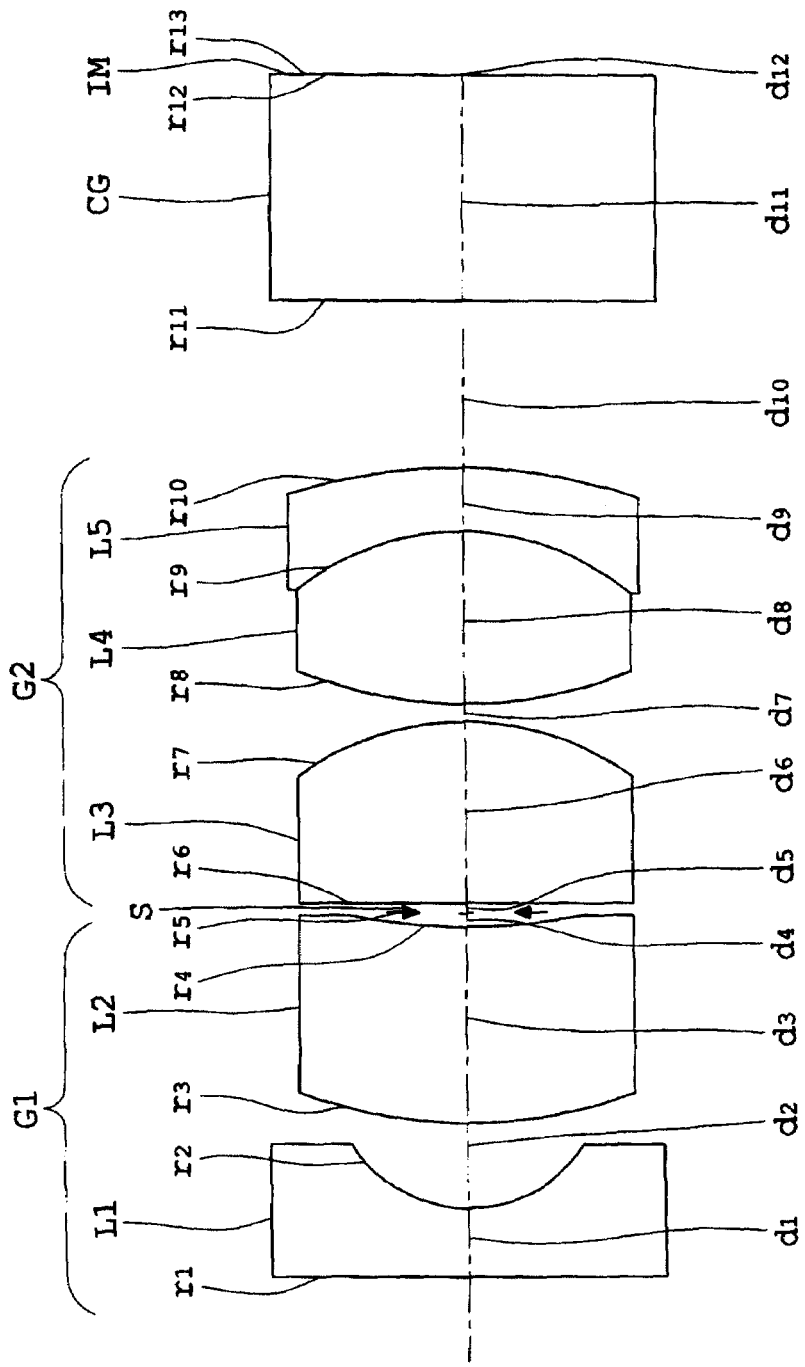

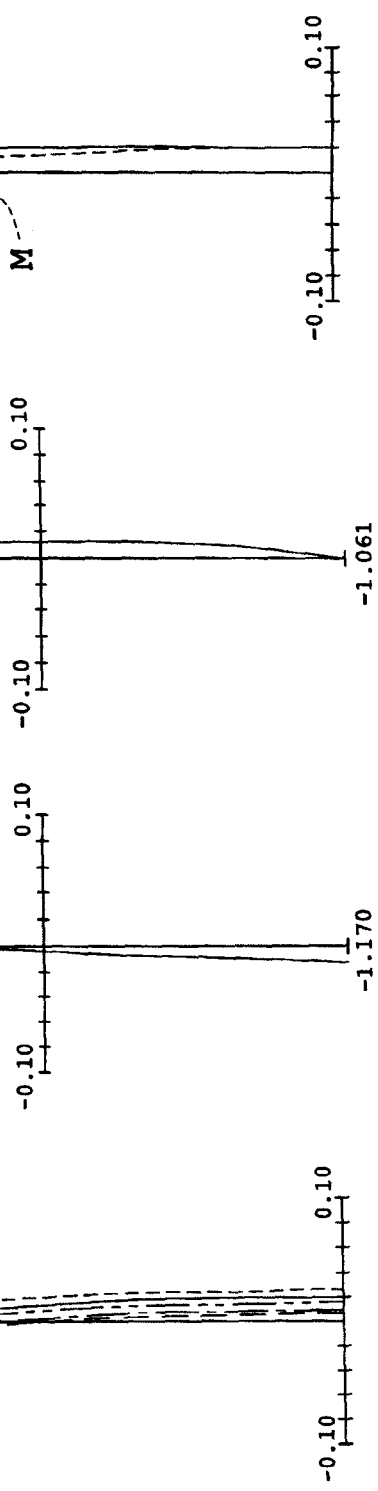

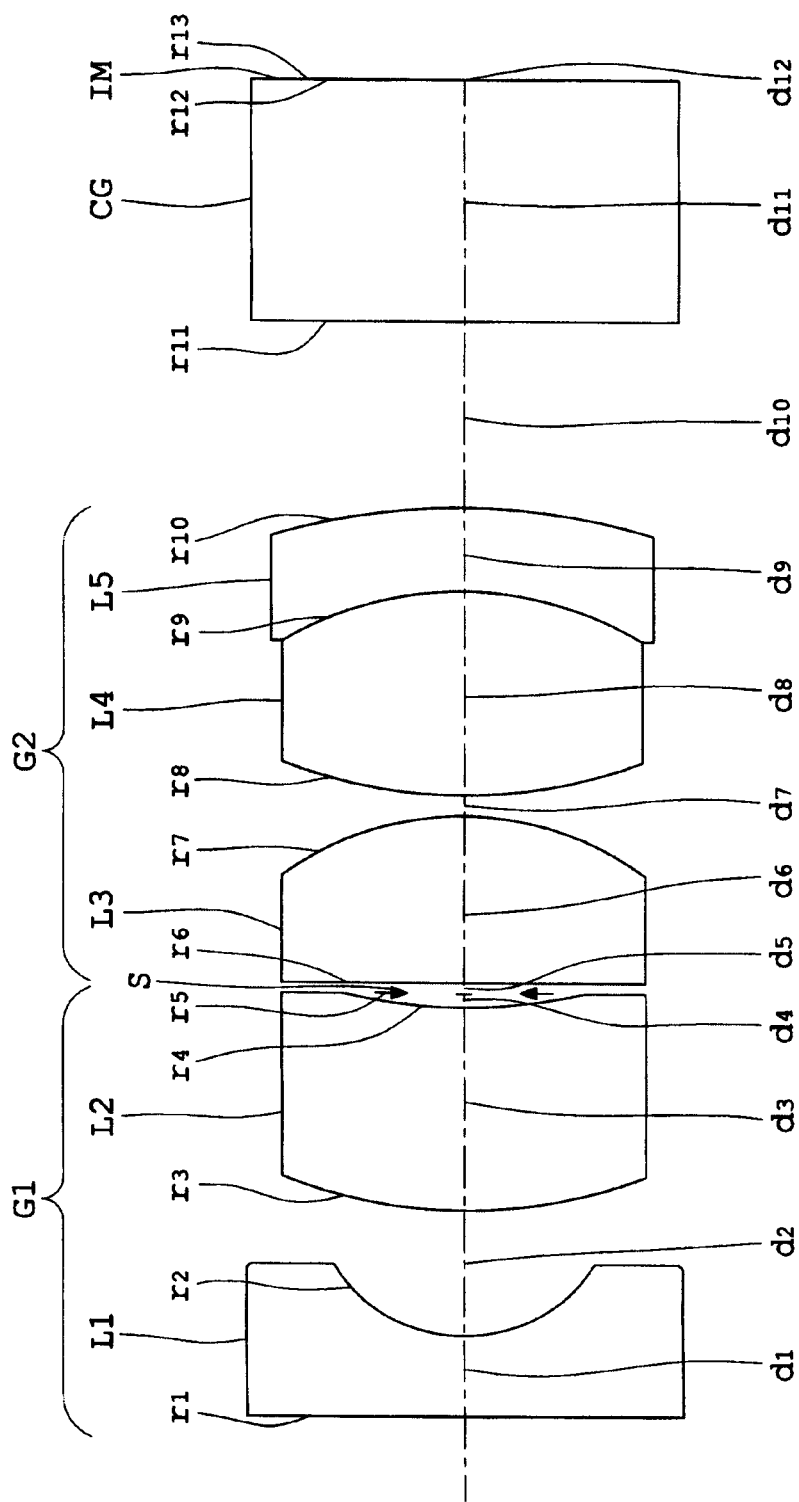

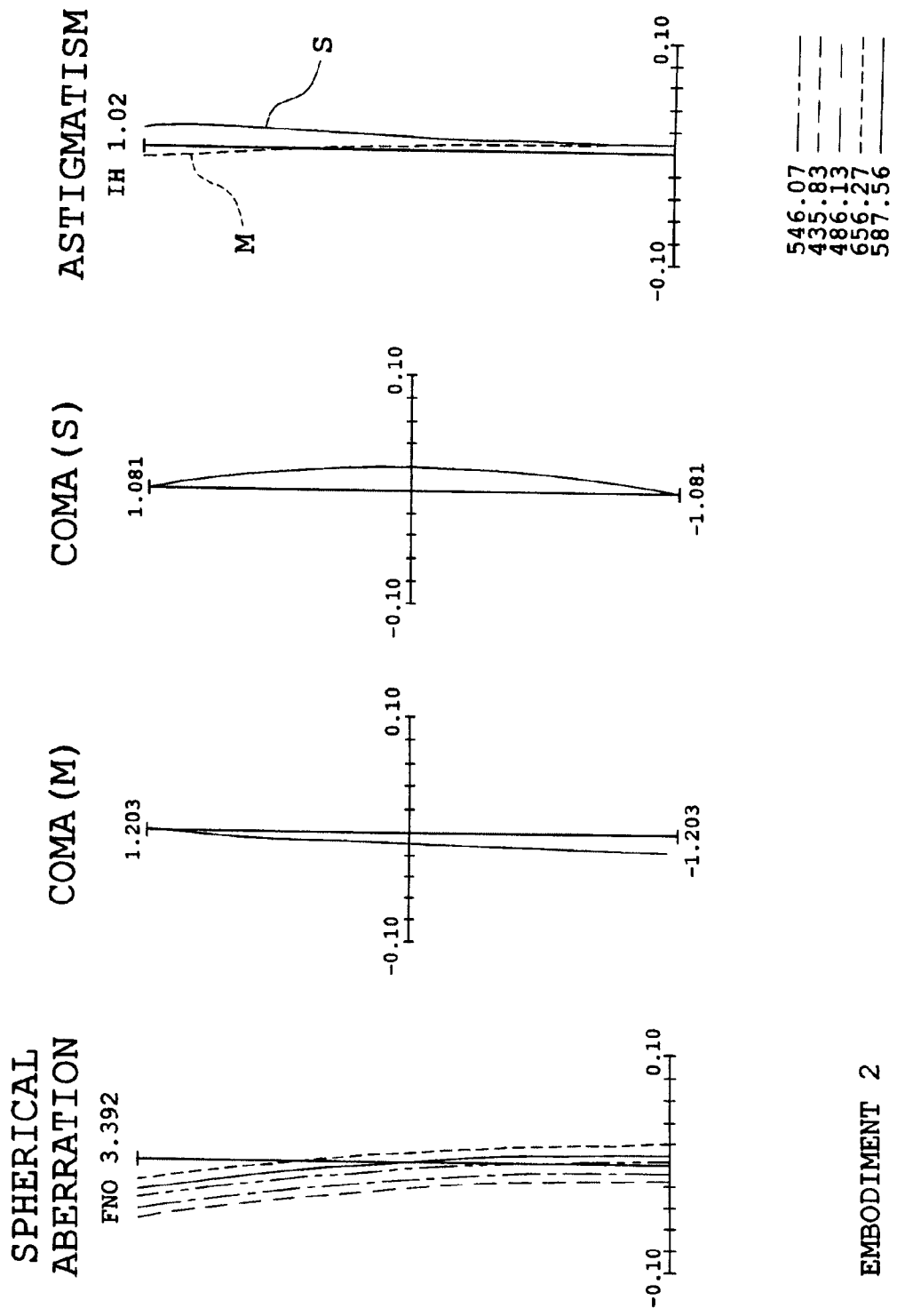

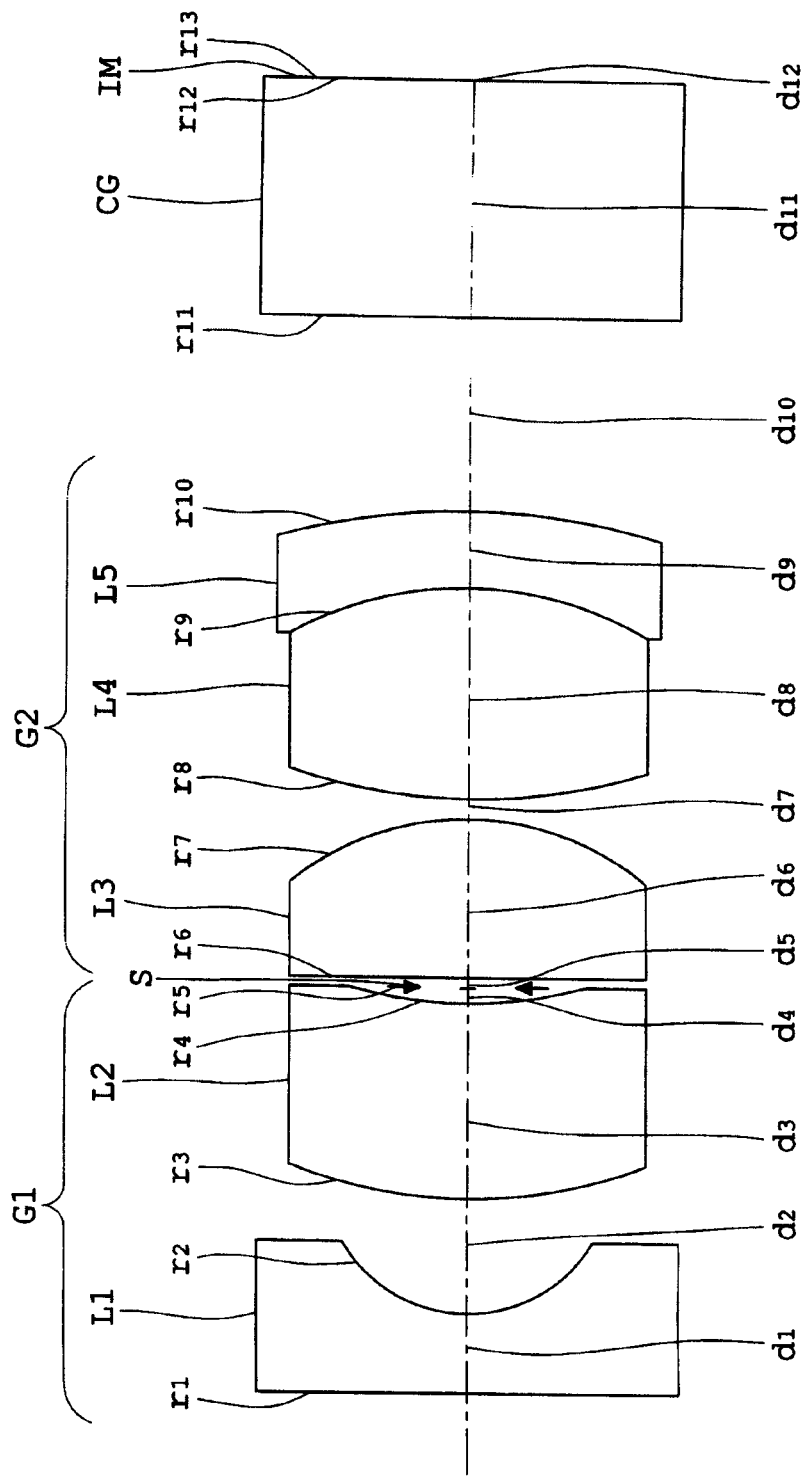

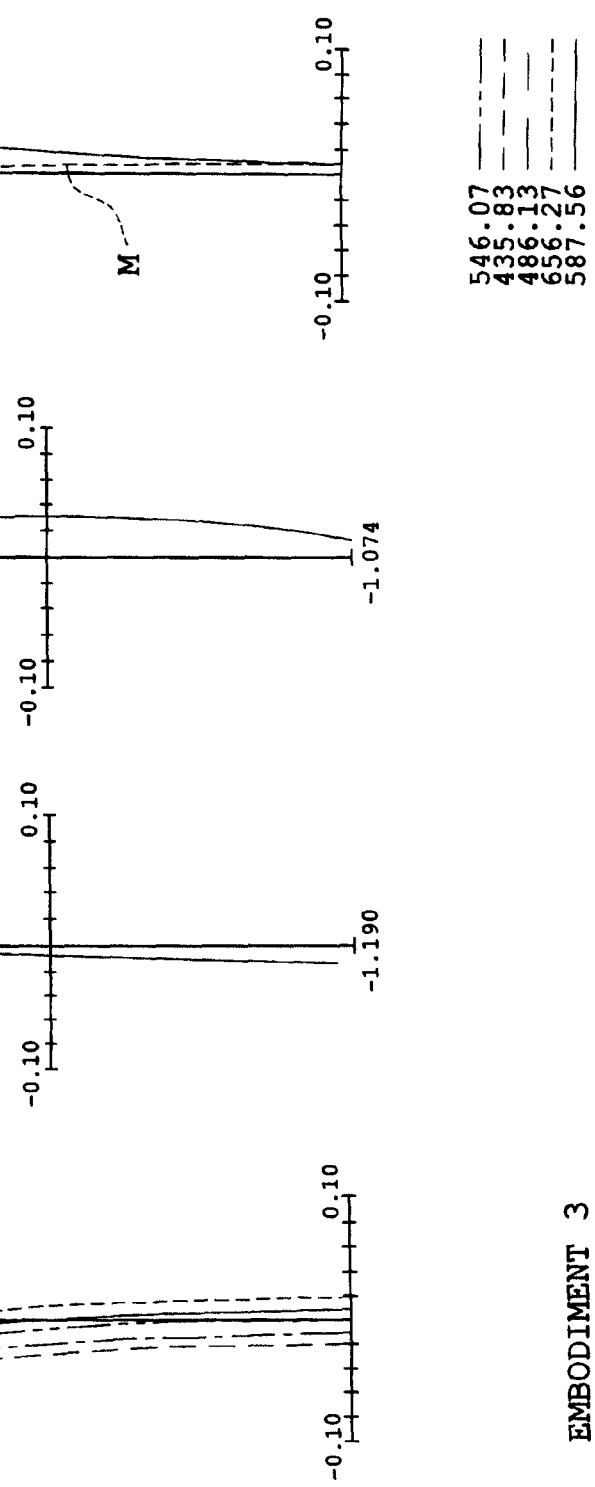

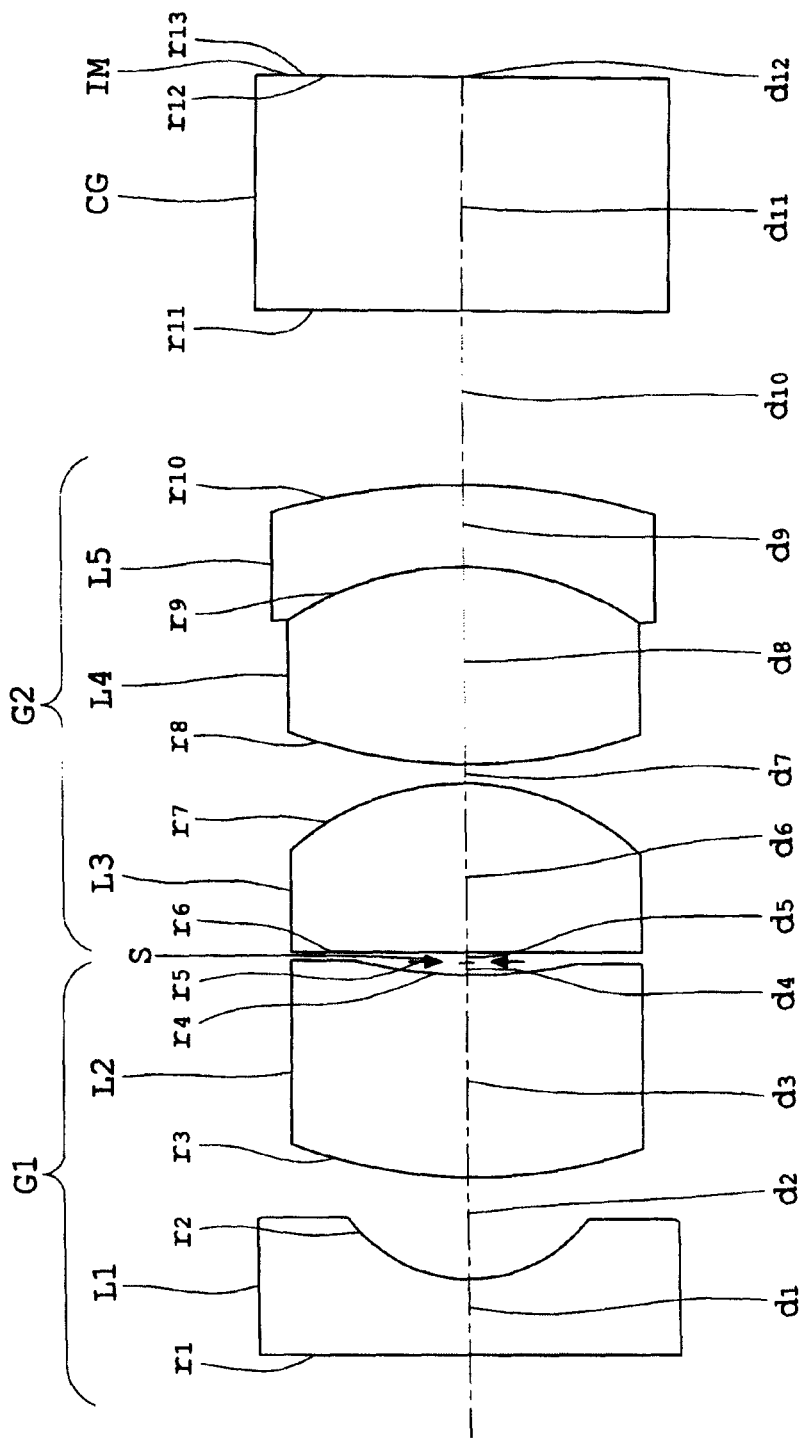
FIG. 7 EMBODIMENT 4

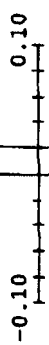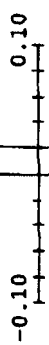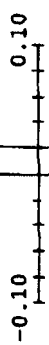

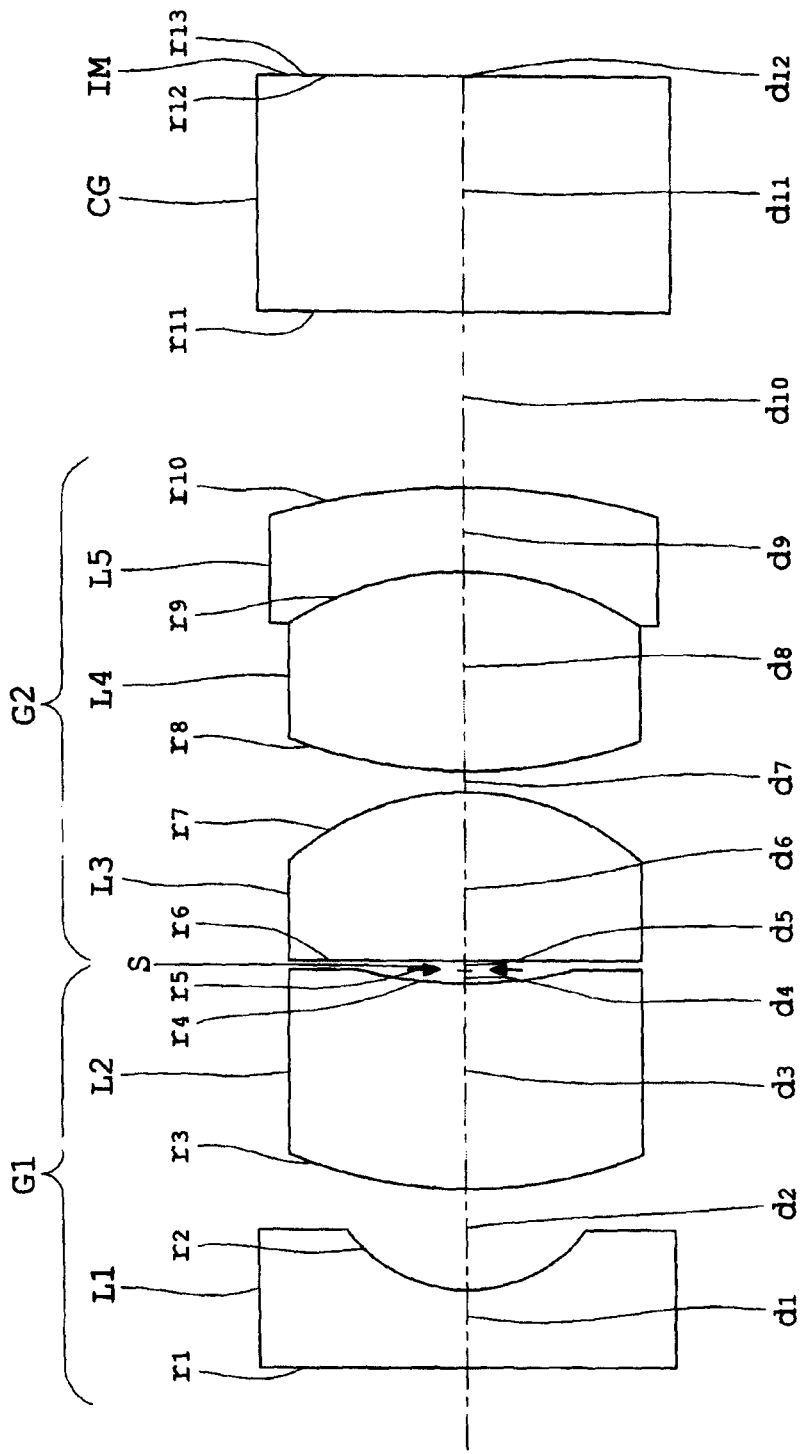

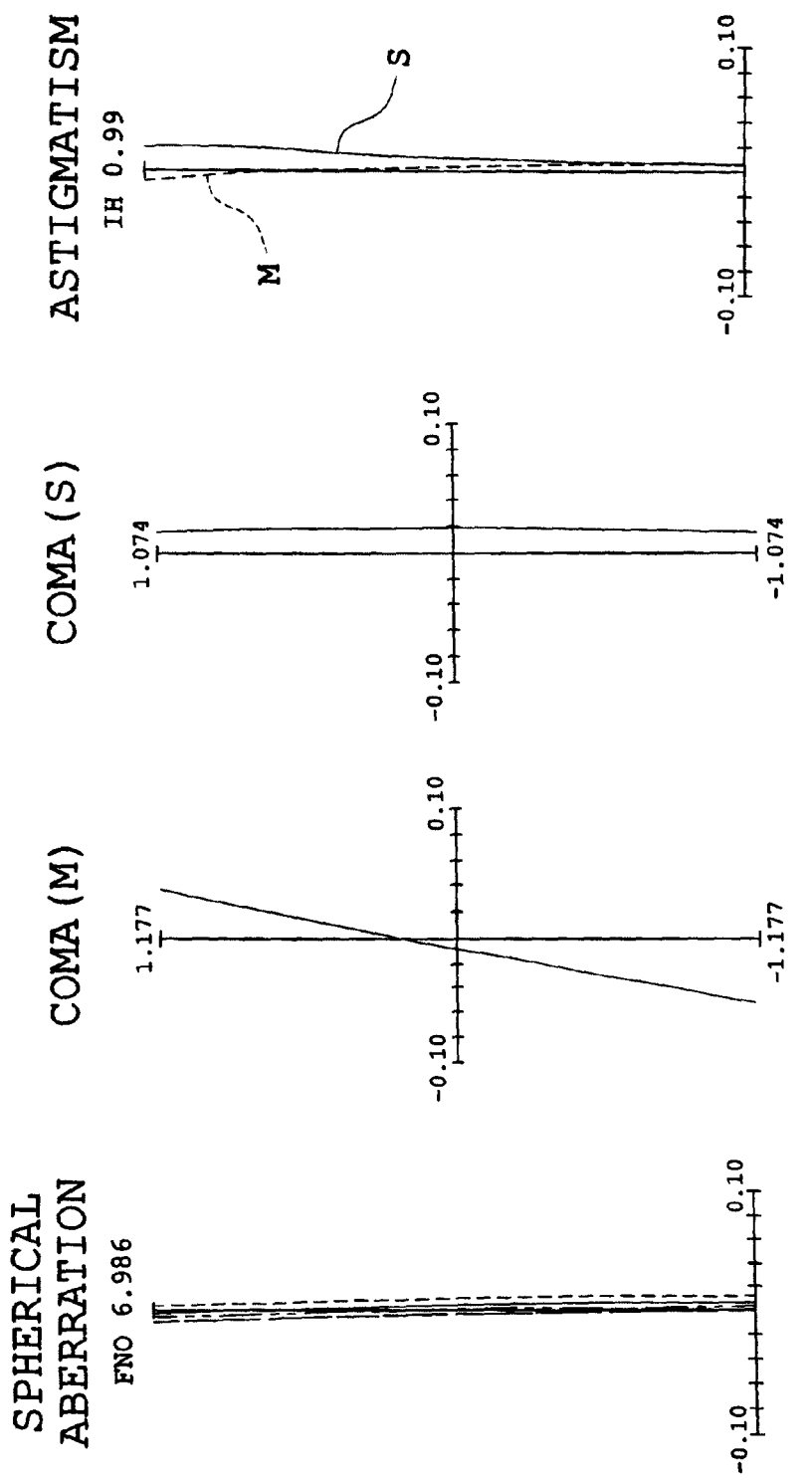

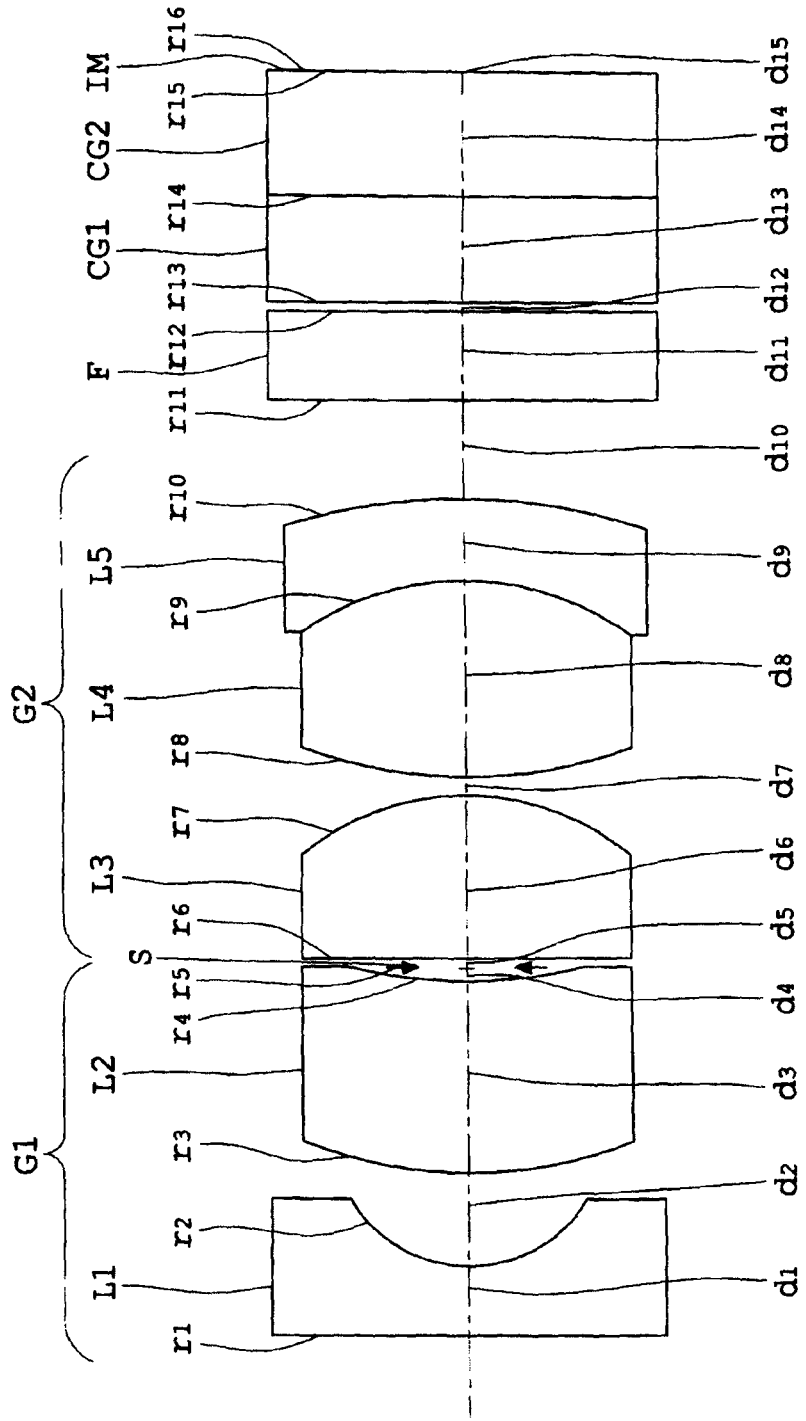

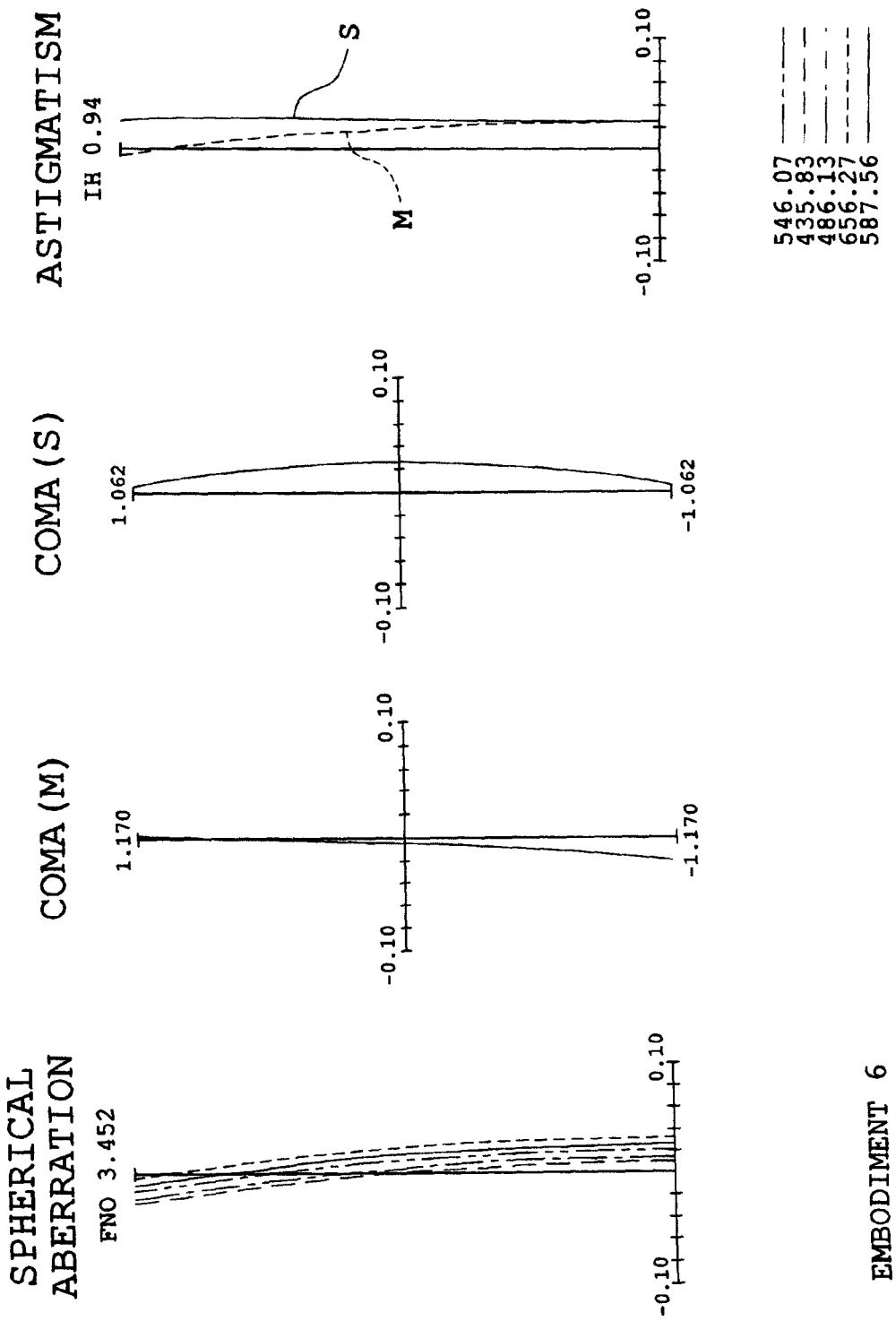

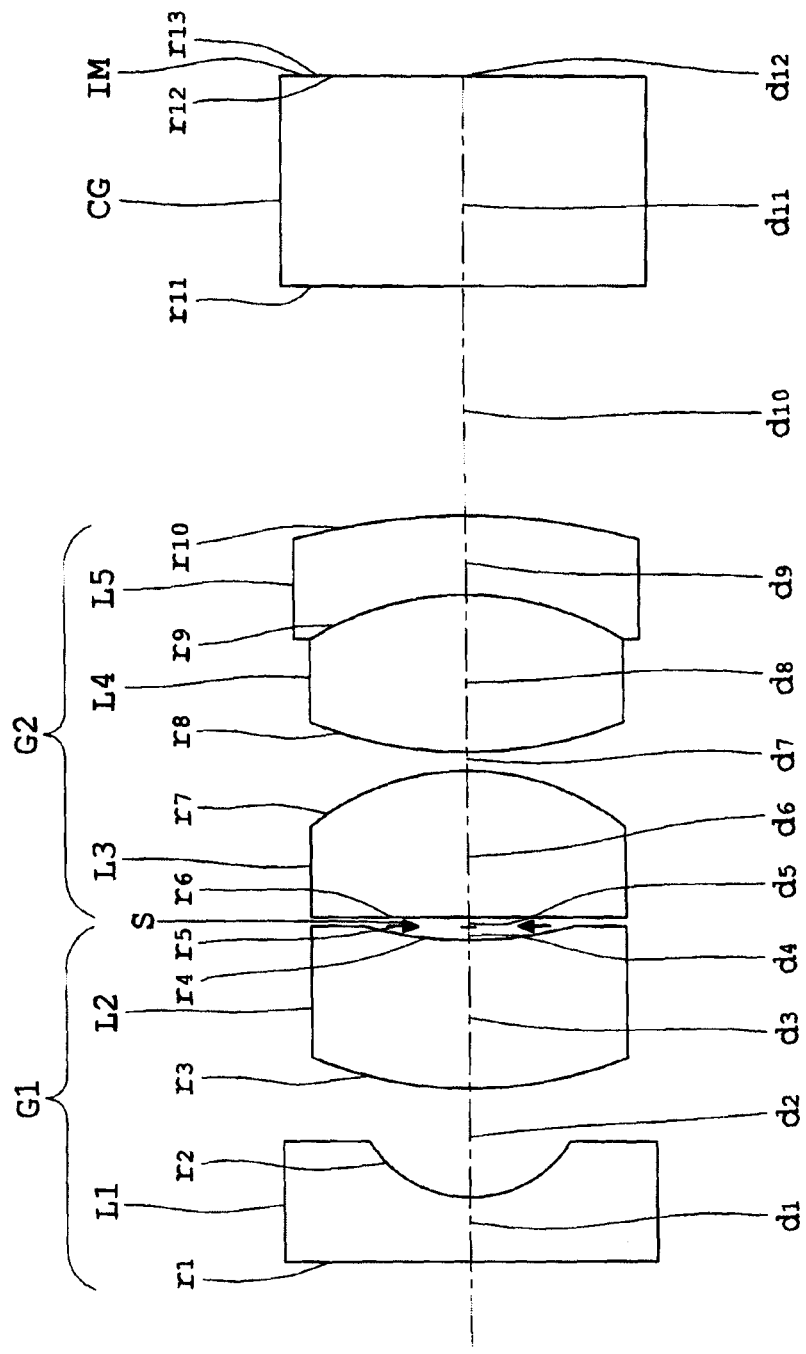

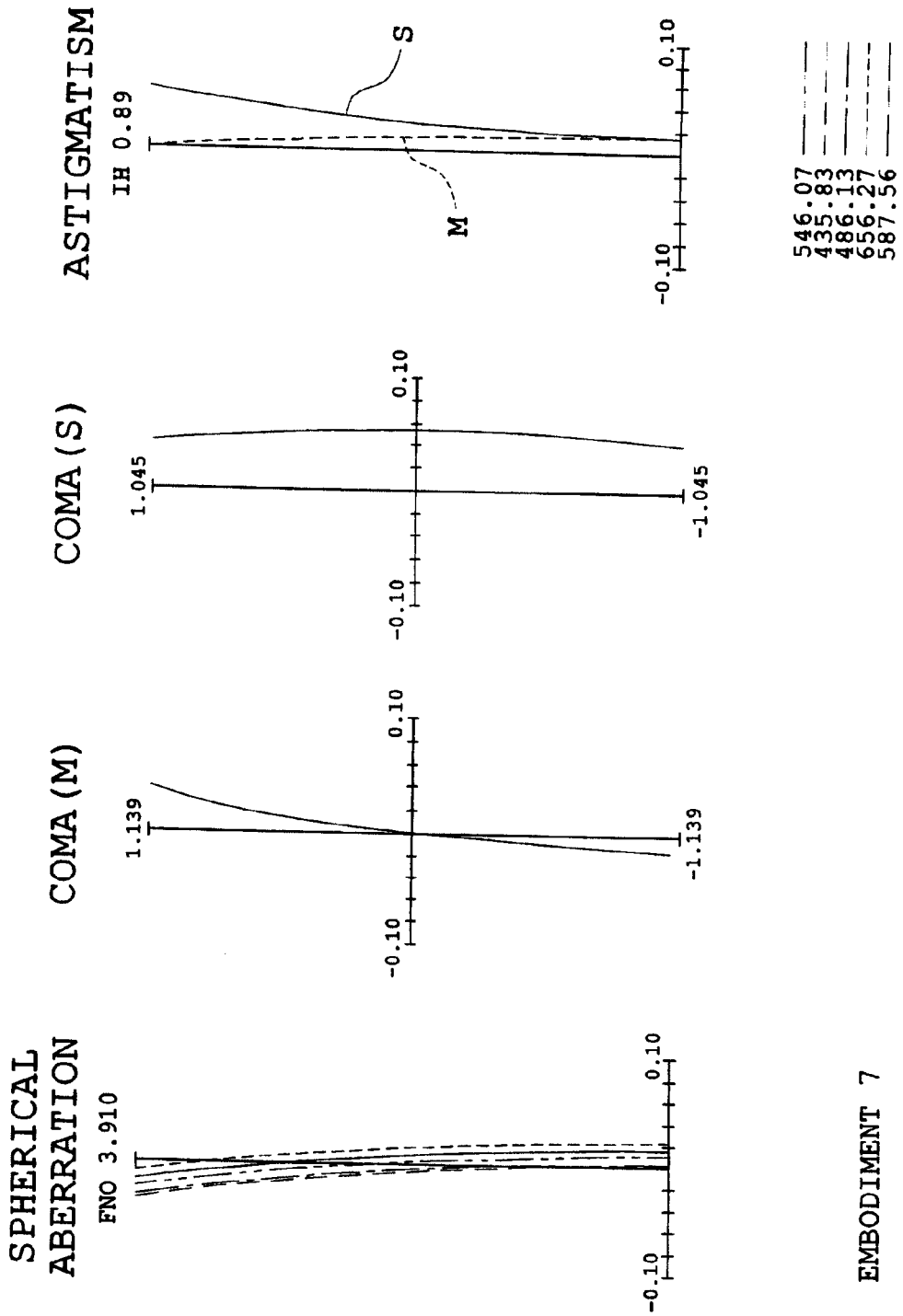

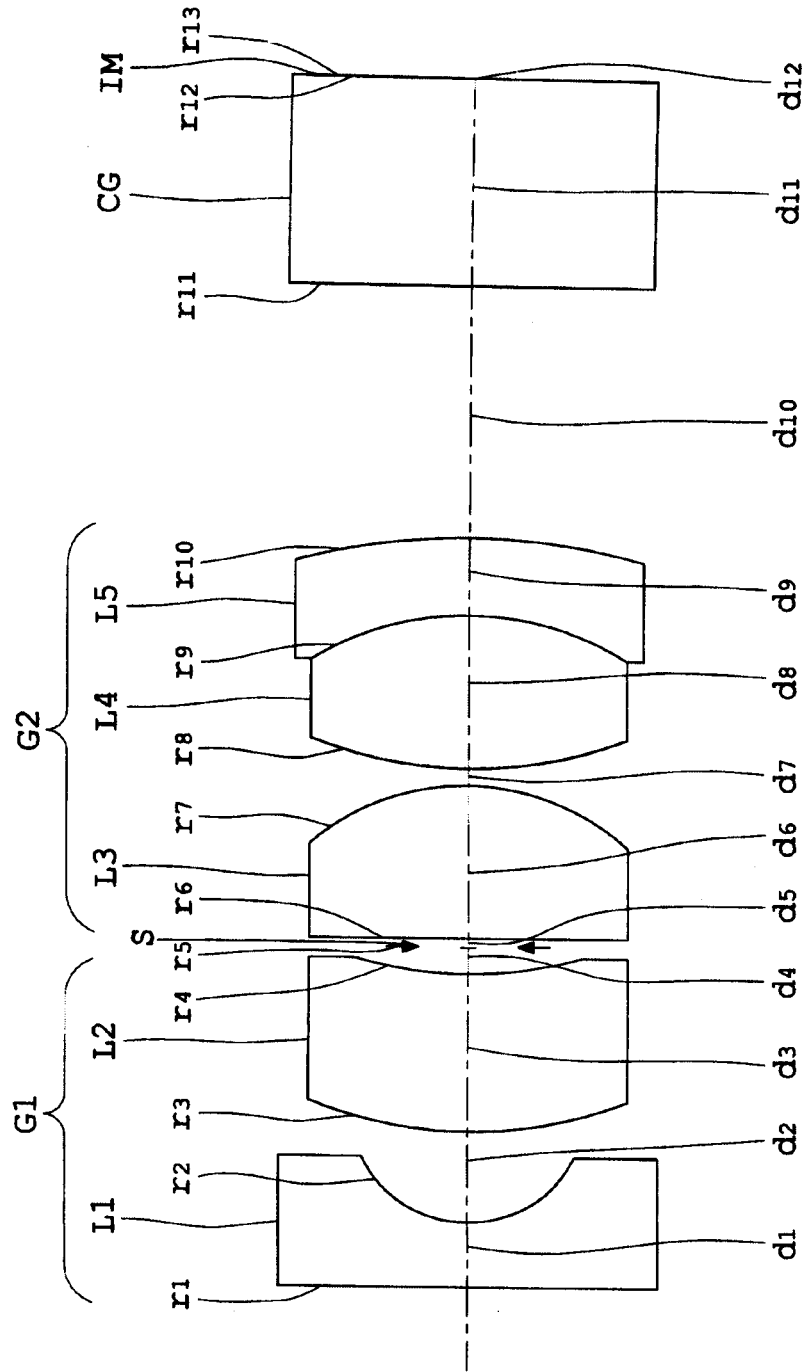

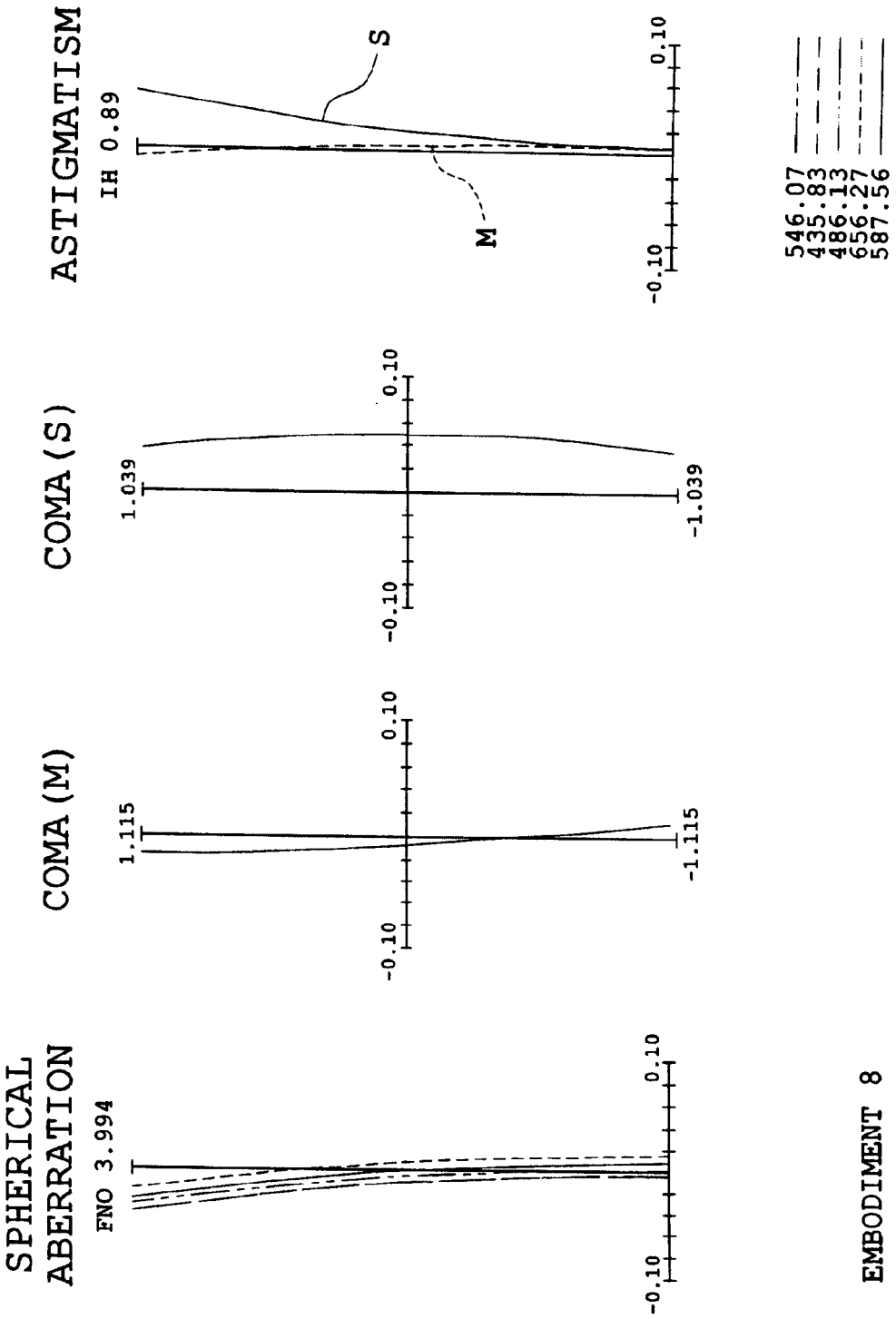

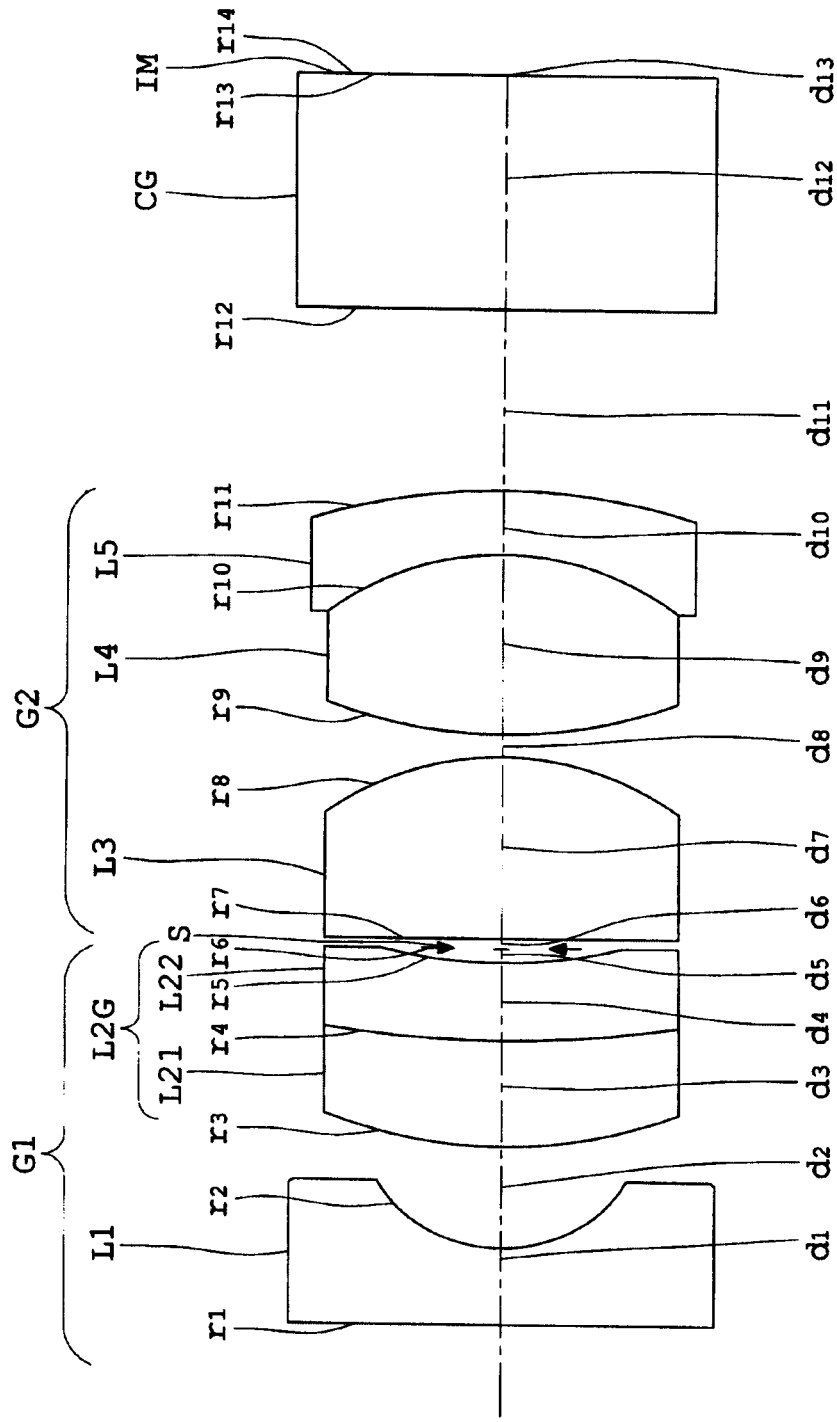

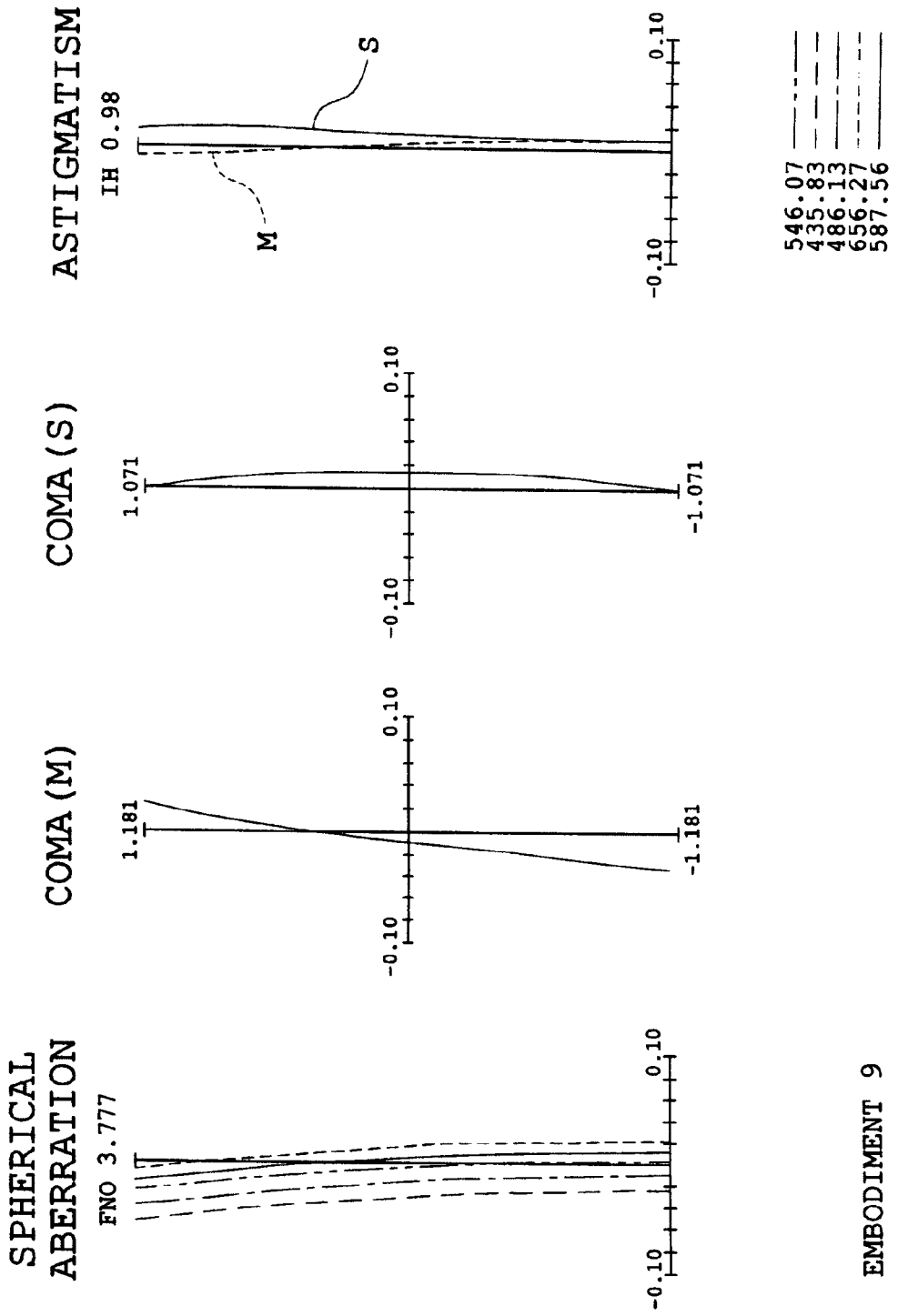

EMBODIMENT 10

EMBODIMENT 11

EMBODIMENT 12

EMBODIMENT 13

EMBODIMENT 14

EMBODIMENT 15

FIG.30A  FIG.30B  FIG.30C  FIG.30D

SPHERICAL ABERRATION
FNO 6.638

COMA (M)
1.157 / -1.157

COMA (S)
1.060 / -1.060

ASTIGMATISM
IH 0.96

S
M 546.07
435.83
486.13
656.27
587.56

EMBODIMENT 15

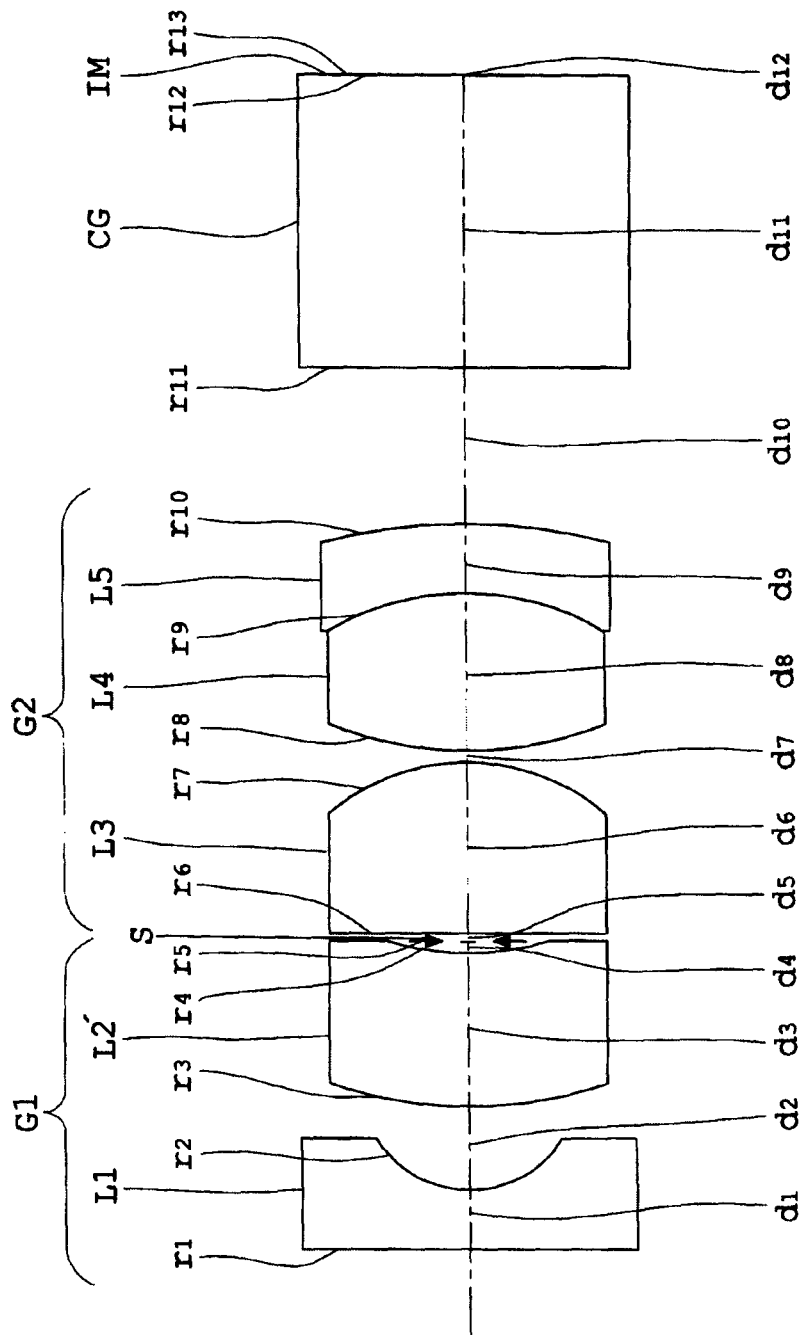

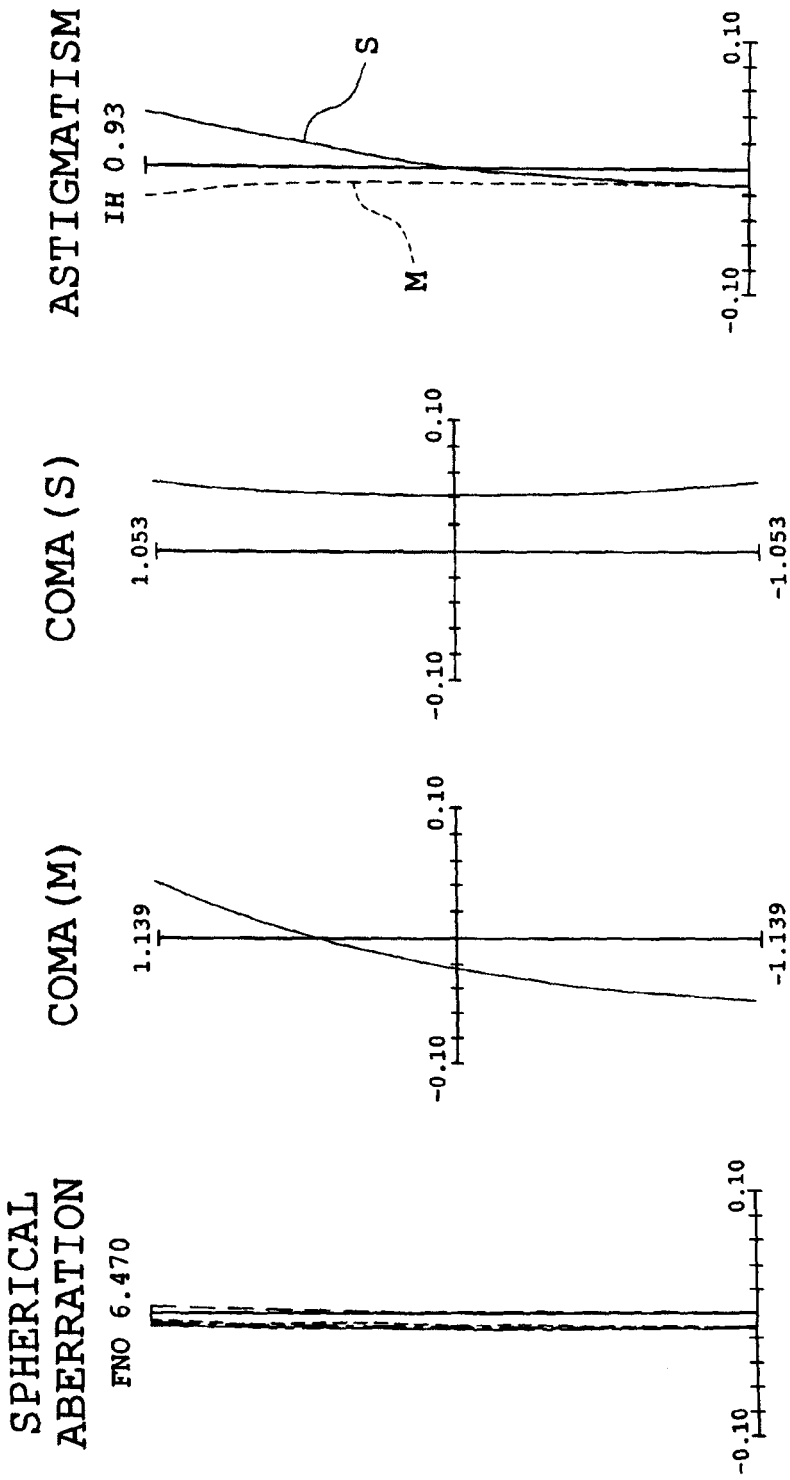

EMBODIMENT 17

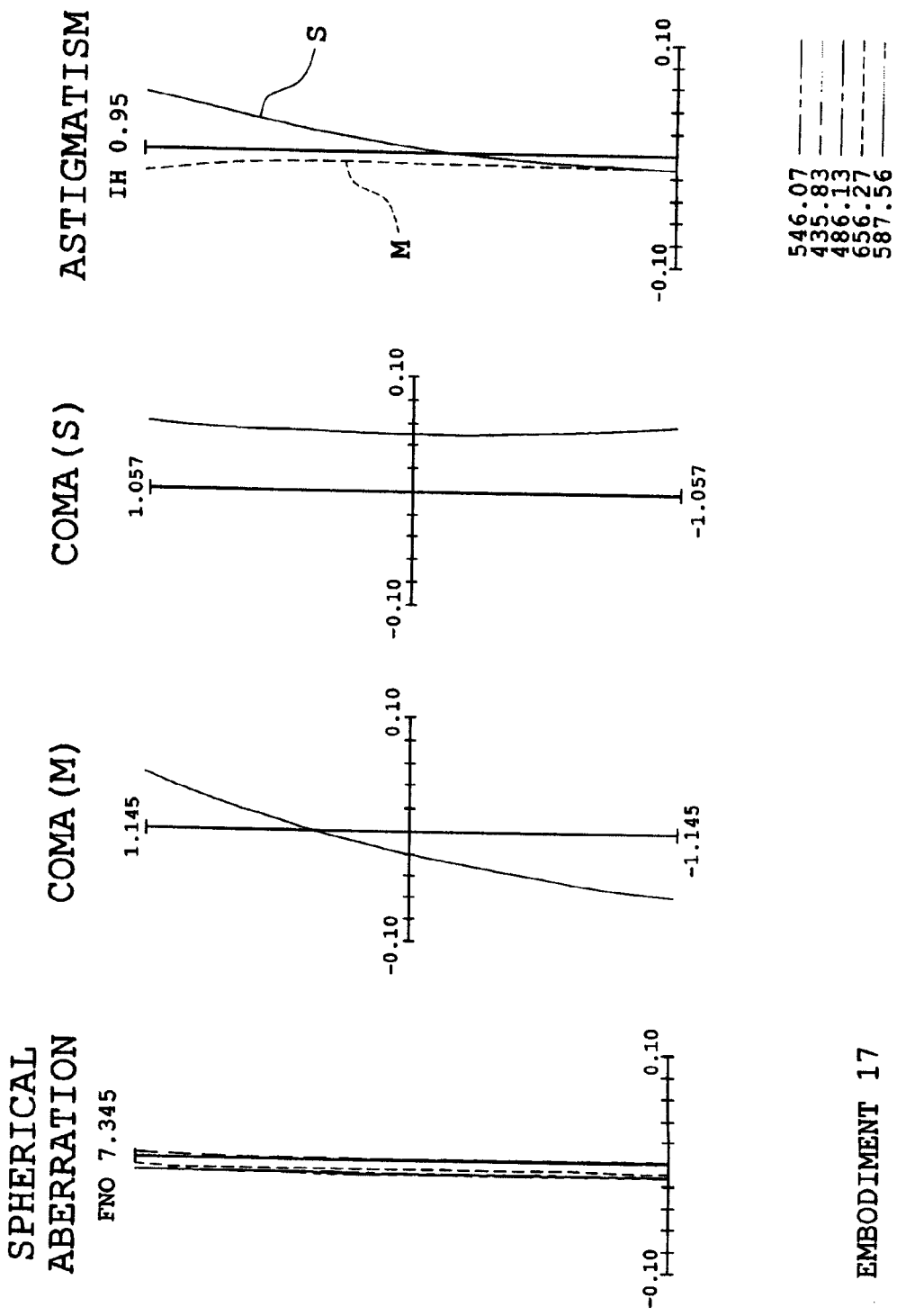

OBJECTIVE LENS FOR ENDOSCOPE

This application claims benefits of Japanese Patent Application No. 2008-069708 filed in Japan on Mar. 18, 2008, the contents of which are hereby incorporated by reference.

BACKGROUND OF THE INVENTION

1. Field of the Invention

The present invention relates to an objective lens used for an endoscope.

2. Description of the Related Art

In the field of medical care, an endoscope is conventionally used to observe a site of a patient that is difficult to externally observe in treating and/or diagnosing the inside of the body of the patient. In recent years, with the reduced diameters of endoscopes typified by nasal endoscopes, small-sized image pickup elements (for example, CCDs and CMOSs) for endoscopes have been developed, with the pixel pitches thereof reduced year by year. Accordingly, objective lenses for endoscopes need to have reduced sizes and to meet optical performance requirements for an increase in the angle of view, aberration correction, prevention of a decrease in the quantity of light, and the like.

Conventionally proposed objective lenses for endoscopes are described in, for example, Japanese Laid-Open Patent Applications 2004-61763, 2004-354888, Hei 8-122632, and Hei 10-20189.

The objective lens for endoscopes described in Japanese Laid-Open Patent Application 2004-61763 is intended to offer a wide angle of view of about 135 to 140 degrees and a required back focus, while properly correcting aberration, particularly the chromatic aberration of magnification to exhibit acceptable optical performance. To accomplish this object, the objective lens is characterized as follows. The objective lens has a four-group, five-lens configuration, that is, the objective lens is composed of a cemented lens $L_{4+5}$ made up of a negative first lens $L_1$ with a concave surface directed toward an image side, a positive second lens $L_2$ with a plane directed toward the image side, a brightness aperture stop, a positive third lens $L_3$ with a plane or a surface of a large radius of curvature directed toward an object side, and a cemented lens including a positive fourth lens $L_4$ with a plane or a surface of a large radius of curvature directed toward the object side and a fifth lens $L_5$ composed of a negative meniscus lens. The first lens $L_1$, the second lens $L_2$, the brightness aperture stop, the third lens $L_3$, and the cemented lens $L_{4+5}$ are arranged in this order so that the first lens $L_1$ is closest to the object. The cemented lens $L_{4+5}$ as a whole has a positive refractive index. The objective lens satisfies conditions (21) to (23):

$$1.50 |d/f1'| < 2.50 \quad (21)$$

$$0.96 < f'/h < 1.04 \quad (22)$$

$$12.0 < f \times (v_4 - v_5)/(Rc \times Bf') \quad (23)$$

where d denotes the distance from the top of the concave surface of the first lens $L_1$ to the brightness aperture stop, f1' denotes the focal length of the first lens $L_1$, h denotes a maximum image height, f denotes the focal length of the whole system, Bf' denotes a back focus, $v_4$ denotes the Abbe number of the positive fourth lens $L_4$, $v_5$ denotes the Abbe number of the negative fifth lens $L_5$, and Rc denotes the absolute value of the radius of curvature of the cemented surface of the cemented lens $L_{4+5}$.

Japanese Laid-Open Patent Application 2004-354888 is intended to provide an objective lens for endoscopes which has a wide angle of view, a small outer diameter, and a first lens with a small maximum ray height and which is further suitable for small-sized CCDs. To accomplish this object, the objective lens is characterized as follows. The objective lens is composed of a front lens group and a rear lens group, between which an aperture stop is arranged. The front lens group is composed of a first lens with a negative refractive power and a second lens with a positive refractive power having a surface of a small radius of curvature directed toward an object; the first lens and the second lens are arranged in this order so that the first lens is closer to the object. The rear lens group is composed of a third lens with a positive refractive power having a surface of a small radius of curvature directed toward the object side, a fourth lens with a positive refractive power, and a fifth lens with a negative refractive power; the fourth lens and the fifth lens are cemented together. When f denotes the composite focal length of the whole system, and f3 denotes the focal length of the third lens, the objective lens satisfies condition (24).

$$2.0 < |f_3/f| < 3.0 \quad (24)$$

The objective lens for endoscopes described in Japanese Patent Laid-Open Hei 8-122632 is intended to enable a reduction in costs required to polish and assemble the lens with proper lens performance maintained. To accomplish this object, the objective lens is characterized as follows. The objective lens includes a negative first lens $L_1$ with a concave surface directed toward an image side, a positive second lens $L_2$ with a plane directed toward the image side, a brightness aperture stop, a positive third lens $L_3$ with a plane directed toward an object side, and a fifth lens $L_5$ made up of a positive fourth lens $L_4$ with a plane directed toward the object side and a negative meniscus lens. The first lens $L_1$, the second lens $L_2$, the brightness aperture stop, the third lens $L_3$, and the fifth lens $L_5$ are arranged in this order so that the first lens $L_1$ is closest to the object, and the fourth lens $L_4$ and the fifth lens $L_5$ make up a cemented lens with a positive refractive power as a whole. Moreover, the objective lens satisfies conditions (25), (26), and (27):

$$0.75 < |f_1 \times Bf/f^2| < 1.45 \quad (25)$$

$$D_i < R_i \quad (26)$$

$$v_2 < 45 \quad (27)$$

where $f_1$ denotes the focal length of the first lens $L_1$, Bf denotes the back focus of the whole system ($L_1$ to $L_5$), f denotes the composite focal length of the whole system ($L_1$ to $L_5$), $D_i$ denotes the central thickness of the lens $L_i$ with a concave surface, $R_i$ denotes the radius of curvature of the convex surface of the lens $L_i$ with the convex surface, and $v_2$ denotes the Abbe number of the second lens $L_2$.

The objective lens for endoscopes described in Japanese Laid-Open Patent Application Hei 10-20189 is intended to inhibit a possible excessive decrease in the radius of curvature of the front group lens and to offer a wide angle of view while correctively reducing distortion with a sharp decrease in the quality of ambient light prevented. To accomplish this object, the objective lens is characterized as follows. The objective lens is composed of a first lens group that as a whole has a negative refractive power, a brightness aperture stop, and a second lens group that as a whole has a positive refractive power, the first lens group, the brightness aperture stop and the second lens group being arranged in this order so that the first lens group is closest to the object. The first lens group is composed of an object-side first lens and an image-side second lens which both have a negative refractive power. The objective lens satisfies conditions (28) and (29):

$$-5.0 < q_1 < -0.9 \quad (28)$$

$$-0.5 < q_2 < 9.0 \quad (29)$$

where $q_1$ denotes the shaping factor of the first lens (=(r2+r1)/(r2−r1), $q_2$ denotes the shaping factor of the second lens (=(r4+r3)/(r4−r3), r1 denotes the radius of curvature of an object-side surface of the first lens, r2 denotes the radius of curvature of an image-side surface of the first lens, r3 denotes the radius of curvature of an object-side of the second lens, and r4 denotes the radius of curvature of an image-side of the second lens.

As described above, the objective lenses for endoscopes are described in, for example, Japanese Laid-Open Patent Applications. 2004-61763, 2004-354888, Hei 8-122632, and Hei 10-20189 all have what is called a retro focus type lens configuration in which the lens closest to the object or the front lens group closer to the object than the aperture stop has a negative refractive power, whereas the rear lens group located closer to the image than the aperture stop has a positive refractive power. The objective lenses further satisfy the predetermined combinations of the conditions shown in conditions (21) to (29).

To offer a somewhat wide angle of view, the retro focus type lens configuration needs to be such that the lens closest to the object includes a concave surface such that the lens has negative refractive power. The retro focus type objective lens, adopted as an objective lens for endoscopes, needs to have a further reduced lens outer diameter in order to meet a demand for a further reduction in the diameter of the endoscope than that of the conventional endoscope, while offering a wider angle of view, which is required for the endoscope. To achieve this, the power of the lens in the front lens group, that is, the negative power of the lens closest to the object, may be increased (i.e., strengthened). However, when the negative power of this lens is increased in association with the further reduced diameter of the endoscope, the curvature of the concave surface of this lens increases. Then, this lens offers degraded processibility and has a high negative refractive power. Thus, possible defocusing of the lens in a frame significantly affects an image. This results in a phenomenon called partial defocusing in which a peripheral portion of the image provided by the endoscope is blurred.

SUMMARY OF THE INVENTION

An objective lens for an endoscope according to the present invention includes a front lens group as a whole having a negative refractive power, a brightness aperture stop, and a rear lens group as a whole having a positive refractive power, the front lens group, the brightness aperture stop, and the rear lens group being arranged in this order so that the front lens group is closest to an object. The front lens group includes a first lens group that is formed of a single lens having a negative refractive power and a second lens group which as a whole has a positive refractive power and in which a surface closest to an image has a concave surface directed toward the image side, the first lens and the second lens group being arranged in this order so that the first lens is closest to the object, and the front lens group satisfies condition (1):

$$|f_0/f_1| \leq 1.1 \quad (1)$$

where $f_0$ denotes the composite focal length of the front lens group, and $f_1$ denotes the focal length of the first lens group.

Furthermore, an objective lens for an endoscope according to the present invention includes a front lens group as a whole having a negative refractive power, a brightness aperture stop, and a rear lens group as a whole having a positive refractive power, the front lens group, the brightness aperture stop, and the rear lens group being arranged in this order so that the front lens group is closest to an object. The front lens group includes a first lens group formed of a single in having a negative refractive power and a second lens group which as a whole has a negative refractive power and in which a surface closest to an image is a concave surface directed toward the image side, the first lens group and the second lens group being arranged in this order so that the first lens group is closest to the object, the second lens group includes a single lens or a cemented lens, and satisfies condition (2):

$$-10 \leq Q1 \leq -2 \quad (2)$$

where Q1 denotes a shaping factor (namely, Q1 equals ($R_2$+$R_1$)/($R_2$−$R_1$) of the second lens group, with $R_1$ denoting the radius of curvature of the surface of the second lens group which is closest to the object, and $R_2$ denoting the radius of curvature of the surface of the second lens group which is closest to the image.

Furthermore, the objective lens for an endoscope according to the second aspect of the present invention preferably satisfies condition (3):

$$|f_0/f_1| < 0.81 \quad (3)$$

where $f_0$ denotes the composite focal length of the front lens group, and $f_1$ denotes the focal length of the first lens group.

Furthermore, in the objective lens for an endoscope according to the present invention, the front lens group preferably includes a positive lens and a cemented lens formed of a positive lens joined to a negative lens, the positive lens and the cemented lens being arranged in this order so that the positive lens is closer to the object.

The present invention enables a further reduction in the diameter of the endoscope, that is, a further reduction in the diameter of the objective lens for an endoscope. Thus, the objective lens for an endoscope according to the present invention, which is of the retro focus type, prevents possible partial defocusing without the need for an increase in the power of the first lens.

The features and advantages of the present invention will become apparent from the following detailed description of the preferred embodiments when taken in conjunction with the accompanying drawings.

BRIEF DESCRIPTION OF THE DRAWINGS

FIG. 1 is a sectional view showing the configuration of an objective lens for an endoscope according to Embodiment 1 of the present invention, the sectional view being taken along an optical axis;

FIGS. 2A, 2B, 2C, and 2D are graphs showing spherical aberration, coma (meridional ray), coma (sagittal ray), and distortion (astigmatism) in an optical system according to Embodiment 1;

FIG. 3 is a sectional view showing the configuration of an objective lens for an endoscope according to Embodiment 2 of the present invention, the sectional view being taken along the optical axis;

FIGS. 4A, 4B, 4C, and 4D are graphs showing spherical aberration, coma (meridional ray), coma (sagittal ray), and distortion (astigmatism) in an optical system according to Embodiment 2;

FIG. 5 is a sectional view showing the configuration of an objective lens for an endoscope according to Embodiment 3 of the present invention, the sectional view being taken along the optical axis;

FIGS. 6A, 6B, 6C, and 6D are graphs showing spherical aberration, coma (meridional ray), coma (sagittal ray), and distortion (astigmatism) in an optical system according to Embodiment 3;

FIG. 7 is a sectional view showing the configuration of an objective lens for an endoscope according to Embodiment 4 of the present invention, the sectional view being taken along the optical axis;

FIGS. 8A, 8B, 8C, and 8D are graphs showing spherical aberration, coma (meridional ray), coma (sagittal ray), and distortion (astigmatism) in an optical system according to Embodiment 4;

FIG. 9 is a sectional view showing the configuration of an objective lens for an endoscope according to Embodiment 5 of the present invention, the sectional view being taken along the optical axis;

FIGS. 10A, 10B, 10C, and 10D are graphs showing spherical aberration, coma (meridional ray), coma (sagittal ray), and distortion (astigmatism) in an optical system according to Embodiment 5;

FIG. 11 is a sectional view showing the configuration of an objective lens for an endoscope according to Embodiment 6 of the present invention, the sectional view being taken along the optical axis;

FIGS. 12A, 12B, 12C, and 12D are graphs showing spherical aberration, coma (meridional ray), coma (sagittal ray), and distortion (astigmatism) in an optical system according to Embodiment 6;

FIG. 13 is a sectional view showing the configuration of an objective lens for an endoscope according to Embodiment 7 of the present invention, the sectional view being taken along the optical axis;

FIGS. 14A, 14B, 14C, and 14D are graphs showing spherical aberration, coma (meridional ray), coma (sagittal ray), and distortion (astigmatism) in an optical system according to Embodiment 7;

FIG. 15 is a sectional view showing the configuration of an objective lens for an endoscope according to Embodiment 8 of the present invention, the sectional view being taken along the optical axis;

FIGS. 16A, 16B, 16C, and 16D are graphs showing spherical aberration, coma (meridional ray), coma (sagittal ray), and distortion (astigmatism) in an optical system according to Embodiment 8;

FIG. 17 is a sectional view showing the configuration of an objective lens for an endoscope according to Embodiment 9 of the present invention, the sectional view being taken along the optical axis;

FIGS. 18A, 18B, 18C, and 18D are graphs showing spherical aberration, coma (meridional ray), coma (sagittal ray), and distortion (astigmatism) in an optical system according to Embodiment 9;

FIGS. 30A, 30B, 30C, and 30D are graphs showing spherical aberration, coma (meridional ray), coma (sagittal ray), and distortion (astigmatism) in an optical system according to Embodiment 15;

FIG. 31 is a sectional view showing the configuration of an objective lens for an endoscope according to Embodiment 16 of the present invention, the sectional view being taken along the optical axis;

FIGS. 32A, 32B, 32C, and 32D are graphs showing spherical aberration, coma (meridional ray), coma (sagittal ray), and distortion (astigmatism) in an optical system according to Embodiment 16;

FIGS. 34A, 34B, 34C, and 34D are graphs showing spherical aberration, coma (meridional ray), coma (sagittal ray), and distortion (astigmatism) in an optical system according to Embodiment 17.

DETAILED DESCRIPTION OF THE PREFERRED EMBODIMENTS

Figure 19:
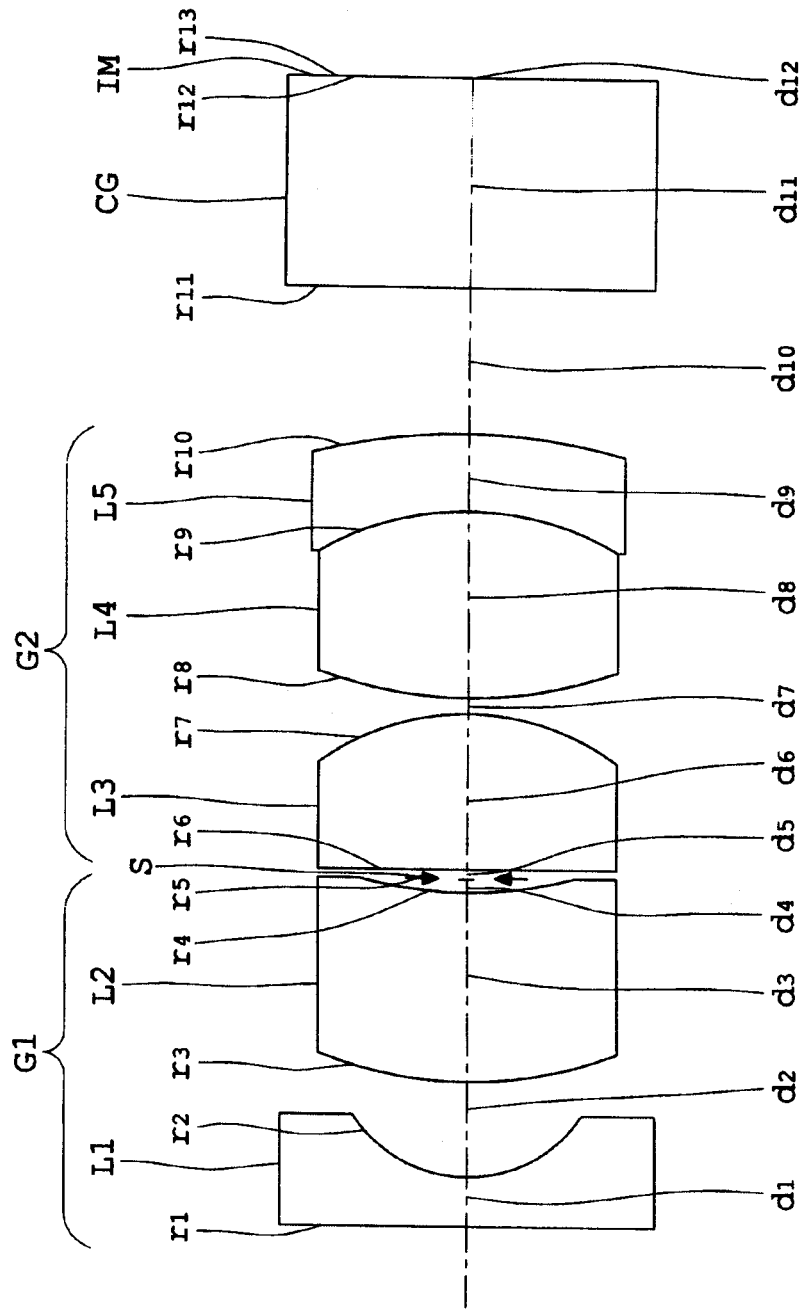
FIG. 19 is a sectional view showing the configuration of an objective lens for an endoscope according to Embodiment 10 of the present invention, the sectional view being taken along the optical axis.
Figure 20:
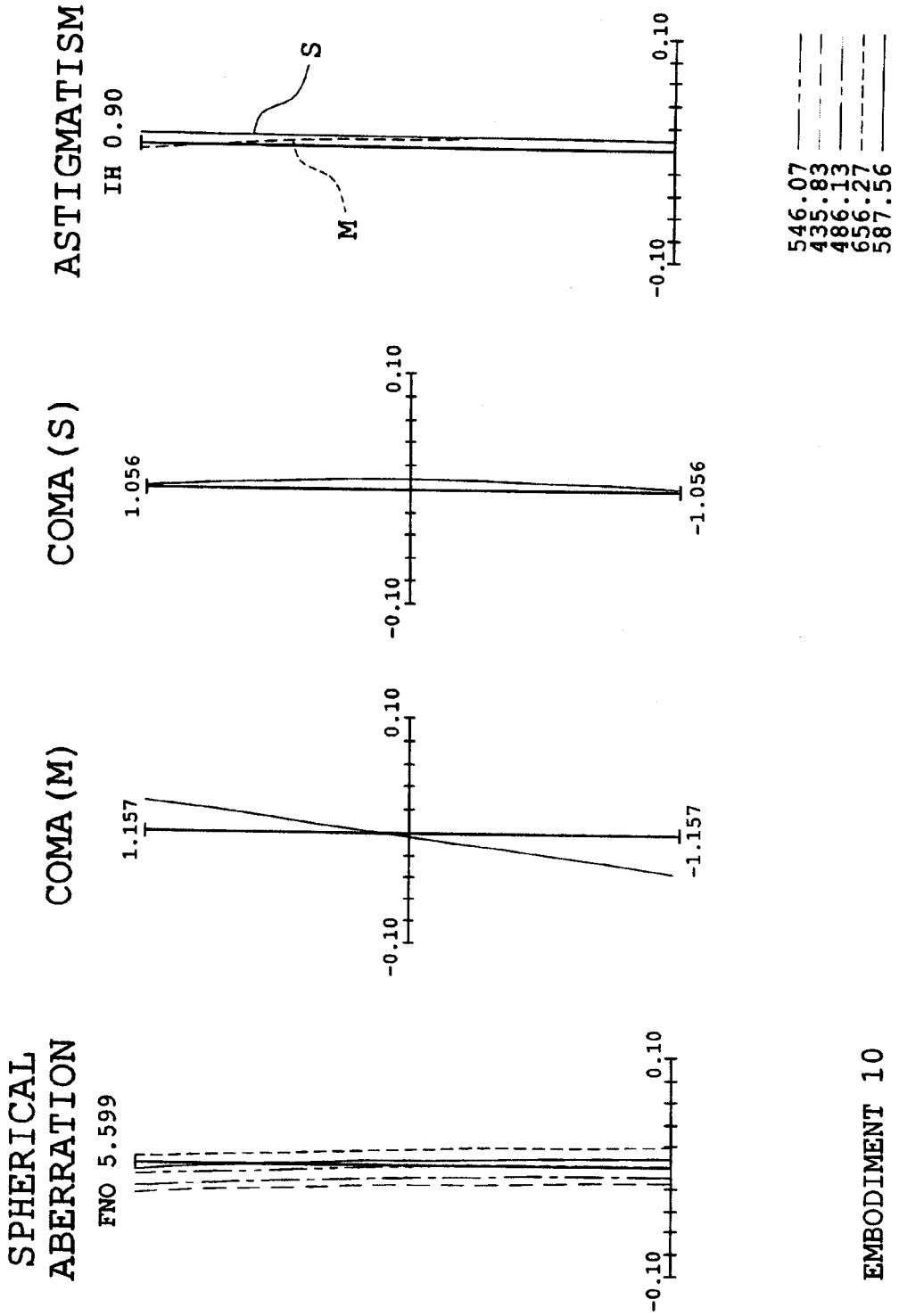
FIGS. 20A, 20B, 20C, and 20D are graphs showing spherical aberration, coma (meridional ray), coma (sagittal ray), and distortion (astigmatism) in an optical system according to Embodiment 10.

Before describing embodiments, the operation and effects of the present invention will be described.

An objective lens for an endoscope according to a first aspect of the present invention is composed of a front lens group as a whole having a negative refractive power, a brightness aperture stop, and a rear lens group as a whole having a positive refractive power, the front lens group, the brightness aperture stop, and the rear lens group being arranged in this order so that the front lens group is closest to an object. The front lens group is composed of a first lens group that is formed of a single lens having a negative refractive power and a second lens group which as a whole has a positive refractive power and in which a surface closest to an image has a concave surface directed toward the image side, the first lens group and the second lens group being arranged in this order so that the first lens group is closest to the object, and the front lens group satisfies condition (1):

$$|f_O/f_1| \leq 1.1 \tag{1}$$

where $f_O$ denotes the composite focal length of the front lens group, and $f_1$ denotes the focal length of the first lens group.

Condition (1) specifies the power distribution of the lenses in the front lens group, which as a whole has a negative refractive power. That is, condition (1) specifies a condition for dispersing negative power required for the front lens group to the second lens group without concentrating the negative power at the first lens group, which is closest to the object. When the negative power is dispersed to the second lens group so as to satisfy condition (1), a smaller lens size and a wider angle of view can be achieved with the power of the first lens group closest to the object kept low. When the value of condition (1) is larger than the upper limit value thereof, the level of the negative power dispersed to the second lens group becomes insufficient. This increases the required curvature of the concave surface of the first lens group object, thus degrading processibility. Furthermore, the influence of decentering of the lens becomes significant, resulting in what is called partial defocusing in which a peripheral portion of an image is blurred.

Japanese Laid-Open Patent Applications 2004-61763, 2004-354888, and Hei 8-122632 all fail to describe a condition corresponding to condition (1). Furthermore, for the objective lenses described in Japanese Laid-Open Patent Applications. 2004-61763, 2004-354888, and Hei 8-122632, the parameter corresponding value of condition (1) described below with reference to Table 2 exceeds the upper limit value thereof. Thus, in Japanese Laid-Open Patent Applications. 2004-61763, 2004-354888, and Hei 8-122632, a further reduction in the diameter of the objective lens for the endoscope may result in partial defocusing.

Now, condition (1) will be described in further detail. The left side $|f_O/f_1|$ of condition (1) can be rewritten as:

$$|f_O/f_1| = |(f_O/f)/(f_1/f)| \tag{1}-1$$

where f denotes the composite focal length of the whole system.

That is, in condition (1), obviously, the numerator is the ratio of the composite focal length of the front lens group to the composite focal length of the whole system. The denominator is the ratio of focal length of the first lens group to the composite focal length of the whole system. Namely, in the objective lenses described in Japanese Laid-Open Patent Applications 2004-61763, 2004-354888, and Hei 8-122632, which correspond to the conventional art, to further reduce the size of the objective lens for endoscopes with the front lens group of the retro focus type, $|f_O/f|$ needs to be decreased. However, reducing the composite focal length $f_O$ of the front lens group is equivalent to reducing the focal length of the first lens group. As a result, $|f_1/f|$ decreases to concentrate the power at the first lens group. Thus, the processibility of the lens that forms the first lens group is degraded, and the adverse effect of lens defocusing becomes significant.

Furthermore, the objective lenses described in Japanese Laid-Open Patent Applications 2004-61763, 2004-354888, and Hei 8-122632, which correspond to the conventional art, fail to be configured such that, in the second lens with positive refractive power that is located in front of the brightness aperture stop, the lens surface closest to the image has a concave surface directed toward the image side as is the case with the first aspect of the present invention. That is, without the power dispersion of the concave surface, the composite focal length of the front lens group is equal to the composite focal length of the first lens of negative refractive power and the second lens of positive refractive power. This can be numerically expressed as:

$$|f_O| > 1.1 \times |f_1|$$

as shown by numerical data in the conventional example in Table 2.

That is, for the objective lenses described in Japanese Laid-Open Patent Applications 2004-61763, 2004-354888, and Hei 8-122632, which correspond to the conventional art, a reduction in $|f_O/f|$ inevitably reduces $|f_1/f|$ so as to increase $|f_O/f_1|$ above 1.1. Thus, when the objective lens is composed of a front lens group having negative refractive power, a brightness aperture stop, and a rear lens group as a whole having positive refractive power, the front lens group, the brightness aperture stop, and the rear lens group are arranged in this order so that the front lens group is closest to an object, and the front lens group is composed of a first lens group formed of a single lens having negative refractive power and a second lens group which as a whole has positive refractive power, and in which the lens surface in the second lens group that is closest to the image is a concave surface directed toward the image side, a small-sized objective lens with a wide angle of view can be provided which ensures the power required for the front lens group, that is, enables a reduction in $|f_O/f|$, while avoiding concentration of the negative refractive power at the first lens that forms the first lens group thereby avoiding a decrease in $|f_1/f|$. That is, condition (1) above is satisfied. By thus dispersing the negative refractive power of the first lens group to the second lens group, an objective lens can be provided in which the first lens group may be formed of a single lens that offers high processibility and which inhibits possible partial defocusing.

Moreover, the objective lens for the endoscope according to the first aspect of the present invention preferably satisfies condition (1'):

$$|f_O/f_1| \leq 1.0 \tag{1'}$$

where $f_O$ denotes the composite focal length of the front lens group, and $f_1$ denotes the focal length of the first lens.

Satisfying condition (1') enables an increase in the level of the dispersion of the negative power to the second lens group in the front lens group, which as a whole has negative refractive power. This in turn enables a reduction in the amount of negative refractive power required of the lens closest to the object and thus enables an increase in the radius of curvature of the concave surface. This further enhances the effect of reducing the adverse effect of defocusing of the lens. Thus, the processibility can be improved, and possible partial defocusing can be inhibited.

Furthermore, an objective lens for an endoscope according to the second aspect of the present invention is composed of a front lens group as a whole having a negative refractive power, a brightness aperture stop, and a rear lens group as a whole having a positive refractive power; the front lens group, the brightness aperture stop, and the rear lens group are arranged in this order so that the front lens group is closest to an object. The front lens group is composed of a first lens group that is formed of a single lens having a negative refractive power and a second lens group which as a whole has a negative refractive power and in which a surface closest to an image has a concave surface directed toward the image side, the first lens group and the second lens group being arranged in this order so that the first lens group is closest to the object, and the second lens group is composed of a single lens or a cemented lens, and satisfies condition (2) above.

Condition (2) relates to the lens form of the second lens group, which as a whole has negative refractive power and in which the lens surface of this lens group closest to the image has a concave surface directed toward the image side. Condition (2) also specifies the power distribution of the lenses in the front lens group, which as a whole has negative refractive power. That is, condition (2) specifies a condition for dispersing the negative power required for the front lens group to the second lens group without concentrating the power at the first lens group (i.e., at the lens closest to the object). Having the second lens group as a whole be of negative refractive power enables an increase in the level of dispersion of the negative refractive power to the second lens group. This in turn enables a reduction in the adverse effect of defocusing of each lens, thus preventing possible partial defocusing.

However, when the value of condition (2) is larger than the upper limit value thereof, although the condition is effective on the power distribution, the power of a concave surface present in the vicinity of the aperture stop becomes excessive. Thus, the curvature of an image surface is excessively corrected, making aberration correction difficult. On the other hand, when the value of condition (2) is smaller than the lower limit value thereof, the effect of dispersing the power of the front lens group to the second lens group is reduced.

Of Japanese Laid-Open Patent Applications. 2004-61763, 2004-354888, Hei 8-122632, and Hei 10-20189, Japanese Laid-Open Patent Application Hei 10-20189 describes the objective lens based on the configuration in which the second lens group in the front lens group has the negative refractive power. However, in the objective lens described in Japanese Laid-Open Patent Application Hei 10-20189, the shaping factor $q_2$ of the second lens is $-0.5 < q_2 < 9.0$ as shown in condition (34) and is thus much larger than the upper limit value of condition (2). The shaping factor larger than the upper limit value of condition (2) excessively increases the power of the concave surface present in the vicinity of the brightness aperture stop. Thus, the curvature of the image surface is excessively corrected, making the aberration correction difficult. Furthermore, when the shaping factor $q_2$ of the second lens has a positive value, the concave surface of a meniscus lens in the second lens group is oriented in the opposite direction as described in Japanese Laid-Open Patent Application Hei 10-20189. In this case, the front lens group, which as a whole has the negative refractive power, is difficult to provide with a strong power. If the front lens group is provided with a power, the power concentrates at the first lens closest to the object. This prevents possible partial defocusing from being inhibited. When the shaping factor is smaller than the lower limit value of condition (2), the power dispersion to the second lens group becomes insufficient. The effects of the second lens group having the negative refractive power are thus reduced.

As described above, Japanese Laid-Open Patent Applications. 2004-61763, 2004-354888, Hei 8-122632, and Hei 10-20189, Japanese Laid-Open Patent Application Hei 10-20189 involve no idea of preventing partial defocusing in the objective lens for endoscopes. This is because in the field of the objective lens for endoscopes, the object of manufacture of the objective lens has been to achieve a reduction in the tolerances of the lens and the frame in parallel with a reduction in the size of the objective lens for endoscopes. However, with the recently sharply reduced sizes of image pick up elements, an optical system is desirably provided which allows possible partial defocusing to be prevented based on the design per se of the objective lens for endoscopes. Furthermore, the application of the present invention to the conventional objective lens for endoscopes not only allows possible partial defocusing in the conventional endoscope optical system to be prevented but also facilitates the processing of the lens closest to the object and the manufacture of the objective lens. Thus, the problems to be solved by the conditions in Japanese Laid-Open Patent Applications. 2004-61763, 2004-354888, Hei 8-122632, and Hei 10-20189, Japanese Laid-Open Patent Application. Hei 10-20189 are different from those to be solved by the condition in the present invention.

Furthermore, the objective lens for the endoscope according to the second aspect of the present invention preferably satisfies condition (3):

$$|f_0/f_1| < 0.81 \tag{3}$$

where $f_0$ denotes the composite focal length of the front lens group, and $f_1$ denotes the focal length of the first lens.

Condition (3) according to the second aspect of the present invention specifies the power distribution of the lenses in the front lens group, which as a whole has the negative refractive power. When the value of condition (3) is larger than the upper limit value thereof, the level of dispersion of the negative power of the front lens group to the second lens group becomes inappropriate. This prevents a reduction in the adverse effect of defocusing of the front lens group.

Here, condition (3) will be described in further detail. As described above, the left side $|f_0/f_1|$ of condition (3) can be rewritten as:

$$|f_0/f_1| = |(f_0/f)(f_1/f)| \tag{1-1}$$

where f denotes the composite focal length of the whole system.

Some of the embodiments described in Japanese Laid-Open Patent Application Hei 10-20189 satisfy condition (3) according to the present invention. However, Table 2, which is referenced when the configuration factors of condition (1)-1, the denominator $|f_1/f|$ and the numerator $|f_0/f|$, are analyzed, shows that in all the embodiments of Japanese Laid-Open Patent Application Hei 10-20189 except Embodiment 3, $|f_0/f|$ is large. This makes the configurations according to the embodiments of Japanese Laid-Open Patent Application Hei 10-20189 different from the configuration on which the second aspect of the present invention is based and in which the front lens group has a strong power. That is, the second aspect of the present invention proposes the configuration in which the level of the power dispersion is increased to eliminate the need to provide the first lens with a high power in spite of the reduced $|f_0/f|$ of the front lens group. Thus, the second aspect of the present invention is much different from the embodiments described in Japanese Laid-Open Patent Application Hei 10-20189.

Furthermore, in Embodiment 3 of Japanese Laid-Open Patent Application Hei 10-20189, the front lens group has a high power, for example, $|f_0/f|=0.544$. However, on the other hand, $|f_1/f|=0.582$. That is, in Embodiment 3 of Japanese Laid-Open Patent Application Hei 10-20189, the first lens is provided with a high power in order to provide the front lens group with a high power. This fails to accomplish the object of providing a small-sized objective lens with a wide angle of view which allows possible partial defocusing to be prevented. Thus, the configuration according to Embodiment 3 of Japanese Laid-Open Patent Application Hei 10-20189 is different from that according to the second aspect of the present invention. Furthermore, in all of Embodiments 8, 9, and 10 described in Japanese Laid-Open Patent Application Sho 61-162021, cited as a conventional example in Patent Document 4, $|f_0/f|$ is large for a similar reason. These embodiments thus have objects, configurations, and effects much different from those of the second aspect of the present invention.

Furthermore, in the objective lens for the endoscope according to the second aspect of the present invention, the negative power of the first lens in the front lens group which is closest to the object is dispersed to the second lens group; the front lens group as a whole has the negative refractive power. However, the objective lens according to the second aspect of the present invention is much different, in the manner of the power dispersion, from an objective lens in which the power is dispersed by dividing the negative lens closest to the object into two or three lenses as in the case of a wide-angle lens typified by a fisheye lens. That is, in the objective lens for the endoscope according to the second aspect of the present invention, the negative power of the first lens closest to the object is dispersed to the vicinity of the brightness aperture stop in the front lens group. Namely, unlike in the case of the power dispersion of the negative lens based on an increase in the number of lenses as typically seen in the fisheye lens, the negative power of the first lens required for the front lens group as a whole is distributed to the whole front lens group.

In the objective lens for endoscope according to the first and second aspects of the present invention the following condition (4) is preferably satisfied:

$$d/f \leq 0.3 \quad (4)$$

where d denotes the surface-to-surface spacing between the surface in the front lens group that is closest to the image and the brightness aperture stop, and f denotes the composite focal length of the whole system. Condition (4) specifies the position of the surface in the second lens group to which the negative power of the first lens in the front lens group which is closest to the object is dispersed.

Furthermore, in the objective lenses for the endoscope according to the first and second aspects of the present invention, the rear lens group, which as a whole has the positive refractive power, is preferably made up of a positive lens and a cemented lens of a positive lens and a negative lens arranged in this order so that the positive lens is closer to the object than the cemented lens. In contrast to the front lens group, which as a whole has the negative refractive power, the rear lens group as a whole requires the positive refractive power in order to allow the focal length to be determined. Distributing the positive power between the single lens and the cemented lens enables chromatic aberration of magnification and coma to be corrected.

Next, Embodiments according to the present invention will be explained by using drawings.

Embodiment 1

FIG. 1 is a sectional view showing the configuration of an objective lens for an endoscope along an optical axis concerning an Embodiment 1 according to the present invention. FIGS. 2A, 2B, 2C, and 2D are graphic charts showing a spherical aberration, a coma aberration (meridional ray), a coma aberration (sagittal ray), and a distortion (astigmatism) in the optical system, respectively. The objective lens for the endoscope of Embodiment 1 is composed of a front lens group G1, a rear lens group G2, and a brightness aperture stop S which is inserted between the front lens group G1 and the rear lens group G2. In FIG. 1, CG is a cover glass, and IM is an image surface. The front lens group G1 has, in order from object side, a first lens having a flat surface directed toward the object side, and a concave surface directed toward an image side; a second lens L2 of a meniscus form, which has positive refractive power, and a concave surface directed toward the image side; and it has negative refractive power as a whole. A rear-lens group G2 comprises a third lens L3 of a plano-concave form which has a flat surface directed toward the object side, and a convex surface directed toward the image side; a fourth lens L4 of bi-convex-form lens; a fifth lens L5 of meniscus form which has negative refractive power and a concave surface directed toward the object side; and it has positive refractive power as a whole. The fourth lens L4 and the fifth lens L5 are joined.

Next, numerical data of optical components which constitutes the objective lens for endoscope of Embodiment 1 are shown. Here, in the lens shown in the sectional drawing in FIG. 1, numbers in r1, r2 . . . , and d1, d2 . . . correspond to the numbers 1, 2 . . . of surface numbers in the following numerical data. In the following numerical data, a refractive index and an Abbe number are values in e line. These are common in other Embodiments.

Numerical Data of Embodiment 1

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 13.5000 | | |
| 1 | ∞ | 0.4488 | 1.88815 | 40.76 |
| 2 | 0.8409 | 0.5065 | | |
| 3 | 2.8385 | 1.2200 | 1.93429 | 18.90 |
| 4 | 4.1922 | 0.0808 | | |
| 5 (S) | ∞ | 0.0539 | | |
| 6 | ∞ | 1.0732 | 1.88815 | 40.76 |
| 7 | −1.6646 | 0.1077 | | |
| 8 | 2.8692 | 1.0234 | 1.59143 | 61.14 |
| 9 | −1.5746 | 0.3739 | 1.93429 | 18.90 |
| 10 | −3.4104 | 0.9899 | | |
| 11 | ∞ | 1.3683 | 1.51825 | 64.14 |
| 12 | ∞ | 0 | | |
| 13 (IM) | ∞ | 0 | | |

| Various data | |
|---|---|
| Focal length | 1.00000 |
| F number | 3.476 |
| Half-angle of view | 63.75045° |
| An image height | 0.932 |
| Full length of lens | 7.2464 |

Embodiment 2

FIG. 3 is a sectional view along an optical axis showing the configuration of an objective lens for endoscope concerning Embodiment 2 of the present invention. FIGS. 4A, 4B, 4C and 4D are graphic charts showing a spherical aberration, a coma aberration (meridional ray), a coma aberration (sagittal ray), and a distortion (astigmatism) in the optical system of Embodiment 2. The objective lens for the endoscope of Embodiment 2 is composed of a front lens group G1, a rear lens group G2, between which a brightness aperture stop S is inserted. In FIG. 3, CG is a cover glass, and IM is an image surface. Fundamental compositions of lenses of the front lens group G1 and the rear lens group G2, are nearly the same to those of Embodiment 1.

Next, numerical data of the optical component which constitutes the objective lens for endoscope of Embodiment 2 will be shown.

Numerical Data of Embodiment 2

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 14.5000 | | |
| 1 | ∞ | 0.4904 | 1.88815 | 40.76 |
| 2 | 0.8882 | 0.8047 | | |
| 3 | 3.1015 | 1.2061 | 1.93429 | 18.90 |
| 4 | 3.1387 | 0.0883 | | |
| 5 (S) | ∞ | 0.0589 | | |
| 6 | ∞ | 1.0418 | 1.88815 | 40.76 |
| 7 | −1.7592 | 0.1177 | | |
| 8 | 3.1784 | 1.2144 | 1.59143 | 61.14 |
| 9 | −2.0159 | 0.4910 | 1.93429 | 18.90 |
| 10 | −3.8580 | 1.0935 | | |
| 11 | ∞ | 1.4713 | 1.51825 | 64.14 |
| 12 | ∞ | 0 | | |
| 13 (IM) | ∞ | 0 | | |

| Various data | |
|---|---|
| Focal length | 1.00000 |
| F number | 3.392 |
| Half-angle of view | 77.94567° |
| Image height | 1.018 |
| Entire length of lens | 8.0781 |

Embodiment 3

FIG. 5 is a sectional view along an optical axis showing the configuration of an objective lens for endoscope concerning Embodiment 3 of the present invention. FIGS. 6A, 6B, 6C, and 6D are graphic charts showing a spherical aberration, a coma aberration (meridional ray), a coma aberration (sagittal ray), and a distortion (astigmatism) respectively in the optical system of Embodiment 3. The objective lens for the endoscope of Embodiment 3 consists of a front lens group G1, and a rear-lens group G2, between which a brightness aperture stop S is inserted. In FIG. 5, CG is a cover glass, and IM is an image surface. Fundamental compositions of lenses of the front lens group G1 and the rear lens group G2 are nearly the same to those of Embodiment 1.

Next, numerical data of the optical component which constitutes the objective lens for endoscope of Embodiment 3 will be shown.

Numerical Data of Embodiment 3

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 14.5000 | | |
| 1 | ∞ | 0.4834 | 1.88815 | 40.76 |
| 2 | 0.8439 | 0.7251 | | |
| 3 | 3.0571 | 1.1844 | 1.93429 | 18.90 |
| 4 | 2.9005 | 0.0870 | | |
| 5 (S) | ∞ | 0.0580 | | |
| 6 | ∞ | 0.9762 | 1.88815 | 40.76 |
| 7 | −1.6525 | 0.1160 | | |
| 8 | 3.3855 | 1.2609 | 1.59143 | 61.14 |
| 9 | −2.1964 | 0.4624 | 1.93429 | 18.90 |
| 10 | −3.8773 | 1.1351 | | |
| 11 | ∞ | 1.4503 | 1.51825 | 64.14 |
| 12 | ∞ | 0 | | |
| 13 (IM) | ∞ | 0 | | |

| Various data | |
|---|---|
| Focal length | 1.00000 |
| F number | 3.719 |
| Half-angle of view | 74.32714° |
| Image height | 1.004 |
| Entire length of lens | 7.9389 |

Embodiment 4

FIG. 7 is a sectional view along an optical axis showing the configuration of an objective lens for endoscope concerning Embodiment 4 of the present invention. FIGS. 8A, 8B, 8C and 8D are graphic charts showing a spherical aberration, a coma aberration (meridional ray), a coma aberration (sagittal ray), and a distortion (astigmatism) in the optical system of Embodiment 4. The objective lens for the endoscope of Embodiment 4 consists of a front lens group G1, a rear lens group G2, and a brightness aperture stop S which is inserted between them. In FIG. 7, CG is a cover glass, and IM is an image surface. Fundamental compositions of lenses of the front lens group G1 and the rear lens group G2 are nearly the same to those of Embodiment 1.

Next, numerical data of the optical components which constitute the objective lens for endoscope of Embodiment 4 will be shown.

Numerical Data of Embodiment 4

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 14.0000 | | |
| 1 | ∞ | 0.4739 | 1.88815 | 40.76 |
| 2 | 0.8758 | 0.6290 | | |
| 3 | 2.9970 | 1.2332 | 1.93429 | 18.90 |
| 4 | 2.6539 | 0.0853 | | |
| 5 (S) | ∞ | 0.0569 | | |
| 6 | ∞ | 1.0114 | 1.88815 | 40.76 |
| 7 | −1.5477 | 0.1137 | | |
| 8 | 3.1013 | 1.1900 | 1.59143 | 61.14 |

-continued

Unit (in mm)

| | | | | |
|---|---|---|---|---|
| 9 | −1.8320 | 0.4844 | 1.93429 | 18.90 |
| 10 | −3.8096 | 1.0343 | | |
| 11 | ∞ | 1.4217 | 1.51825 | 64.14 |
| 12 | ∞ | 0 | | |
| 13 (IS) | ∞ | 0 | | |

Various data

| | |
|---|---|
| Focal length | 1.00000 |
| F number | 6.981 |
| Half-angle of view | 66.22873° |
| Image height | 0.952 |
| Entire length of lens | 7.7338 |

Embodiment 5

FIG. 9 is a sectional view along an optical axis showing the configuration of an objective lens for endoscope concerning Embodiment 5 of the present invention. FIGS. 10A, 10B, 10C and 10D are graphic charts showing a spherical aberration, a coma aberration (meridional ray), a coma aberration (sagittal ray), and a distortion (astigmatism) in the optical system of Embodiment 5. The objective lens for the endoscope of Embodiment 5 consists of a front lens group G1, a rear lens group G2, between which a brightness aperture stop S is inserted. In FIG. 9, CG is a cover glass, and IM is an image surface. Fundamental compositions of lenses of the front lens group G1 and the rear lens group G2 are nearly the same to those of Embodiment 1.

Next, the numerical data of the optical components which constitute an objective lens for endoscope of Embodiment 5 will be shown.

Numerical Data of Embodiment 5

In the following surface data, S denotes aperture stop, and IM denotes image surface.

Unit (in mm)

Surface data

| Surface number | Radius of curvature | Surface interval | Refractive index | Abbe number |
|---|---|---|---|---|
| Object surface | ∞ | 14.0000 | | |
| 1 | ∞ | 0.4788 | 1.88815 | 40.76 |
| 2 | 0.8848 | 0.6354 | | |
| 3 | 3.0278 | 1.2459 | 1.93429 | 18.90 |
| 4 | 2.5854 | 0.0862 | | |
| 5 (S) | ∞ | 0.0575 | | |
| 6 | ∞ | 1.0218 | 1.88815 | 40.76 |
| 7 | −1.5417 | 0.1149 | | |
| 8 | 3.1331 | 1.2022 | 1.59143 | 61.14 |
| 9 | −1.8508 | 0.4893 | 1.93429 | 18.90 |
| 10 | −3.8487 | 1.0449 | | |
| 11 | ∞ | 1.4172 | 1.51825 | 64.14 |
| 12 | ∞ | 0 | | |
| 13 (IM) | ∞ | 0 | | |

Various data

| | |
|---|---|
| Focal length | 1.00000 |
| F number | 6.986 |
| Half angle of view | 72.43092° |
| Image height | 0.994 |
| Entire length of lens | 7.7940 |

Embodiment 6

FIG. 11 is a sectional view along an optical axis showing the configuration of an objective lens for endoscope concerning Embodiment 6 of the present invention. FIGS. 12A, 12B, 12C, and 12D are graphic charts showing a spherical aberration, a coma aberration (meridional ray), a coma aberration (sagittal ray), and a distortion (astigmatism) in the optical system of Embodiment 6, respectively. The objective lens for endoscope of Embodiment 6 is composed of a front lens group G1, a rear lens group G2, and a brightness aperture stop S which is disposed between the front lens group G1 and the rear lens group G2. In FIG. 11, F is an infrared-cut filter, CG1 is a cover glass. CG2 is a cover glass of CCD and IM is an image surface. Fundamental compositions of lenses of the front lens group G1 and the rear lens group G2 are nearly the same to those of Embodiment 1.

In Embodiment 6, an infrared cut filter F is arranged in a space from the rear lens group G2 to an image surface. Furthermore, YAG laser cut coating is applied to one of filter surfaces of this infrared cut filter for a laser treatment used in endoscope operation. On another surface, YAG laser cut coating, LD laser cut coating, or other functional coatings can be applied. Furthermore, a functional coating can be made to both surfaces. Furthermore, merely a reflection protecting coating just like a multi-coating can be applied.

In Embodiment 6, although the infrared cut filter was inserted, other functional filters can be inserted. For example, by inserting a color filter instead of the infrared cut filter, it is possible to change to color reproduction of an image of endoscope. Moreover, in Embodiment 6, although a filter and three cover glasses are inserted in the space from the rear lens group G2 to the image side, the number of them is not restricted. That is, if there is enough space for arrangement, for example, two sheets, or three sheets of the infrared cut filter may be inserted. Or two sheets or three sheets of the filter with different functions may be inserted. For example, an infrared cut filter and a notch filter may be inserted simultaneously. Moreover, for example, one infrared cut filter, one color filter, and one notch filter may be inserted. Of course, it can be replaced by any filter as long as it is a functional filter.

Next, numerical data of optical components which constitutes the objective lens for endoscope of Embodiment 6 will be shown.

Numerical Data of Embodiment 6

In the following surface data, S denotes aperture stop, and IM denotes image surface.

Unit (in mm)

Surface data

| Surface number | Radius of curvature | Surface interval | Refractive index | Abbe number |
|---|---|---|---|---|
| Object surface | ∞ | 13.5000 | | |
| 1 | ∞ | 0.4527 | 1.88815 | 40.76 |
| 2 | 0.8365 | 0.5704 | | |
| 3 | 2.8627 | 1.1589 | 1.93429 | 18.90 |
| 4 | 3.2593 | 0.0815 | | |
| 5 (S) | ∞ | 0.0543 | | |
| 6 | ∞ | 0.9959 | 1.88815 | 40.76 |
| 7 | −1.5826 | 0.1086 | | |
| 8 | 3.0728 | 1.1589 | 1.59143 | 61.14 |
| 9 | −1.7691 | 0.4889 | 1.93429 | 18.90 |

-continued

Unit (in mm)

| 10 | −3.5508 | 0.5794 | | |
| 11 | ∞ | 0.5432 | 1.51965 | 75.00 |
| 12 | ∞ | 0.0543 | | |
| 13 | ∞ | 0.6337 | 1.51825 | 64.14 |
| 14 | ∞ | 0.7470 | 1.61354 | 50.50 |
| 15 | ∞ | 0 | | |
| 16 (IM) | ∞ | 0 | | |

Various data

| Focal length | 1.00000 |
|---|---|
| F number | 3.452 |
| Half-angle of view | 64.92624° |
| Image height | 0.940 |
| Entire length of lens | 7.6277 |

Embodiment 7

FIG. 13 is a sectional view along an optical axis showing the configuration of an objective lens for endoscope concerning Embodiment 7 of the present invention. FIGS. 14A, 14B, 14C, and 14D are graphic charts showing a spherical aberration, a coma aberration (meridional ray), a coma aberration (sagittal ray), and a distortion (astigmatism) in the optical system of Embodiment 7, respectively.

The objective lens for endoscope of Embodiment 7 is composed of a front lens group G1, a rear lens group G2, and a brightness aperture stop S which is disposed between the front lens group G1 and the rear lens group G2. In FIG. 13, CG is a cover glass, and IM is an image surface. Fundamental compositions of lenses of the front lens group G1 and the rear lens group G2 are nearly the same to those of Embodiment 1.

Next, numerical data of optical components which constitutes the objective lens for endoscope of Embodiment 7 will be shown.

Numerical Data of Embodiment 7

In the following surface data, S denotes aperture stop, and IM denotes image surface.

Unit (in mm)

Surface data

| Surface number | Radius of curvature | Surface interval | Refractive index | Abbe number |
|---|---|---|---|---|
| Object surface | ∞ | 15.5000 | | |
| 1 | ∞ | 0.4269 | 1.88815 | 40.76 |
| 2 | 0.7121 | 0.6587 | | |
| 3 | 2.6195 | 0.9112 | 1.93429 | 18.90 |
| 4 | 2.5478 | 0.0768 | | |
| 5 (S) | ∞ | 0.0512 | | |
| 6 | ∞ | 0.8931 | 1.88815 | 40.76 |
| 7 | −1.4367 | 0.1025 | | |
| 8 | 2.7399 | 0.9497 | 1.51825 | 64.14 |
| 9 | −1.7100 | 0.4611 | 1.93429 | 18.90 |
| 10 | −3.5666 | 1.3700 | | |
| 11 | ∞ | 1.2808 | 1.51825 | 64.14 |
| 12 | ∞ | 0 | | |
| 13 (IM) | ∞ | 0 | | |

Various data

| Focal length | 1.00000 |
|---|---|
| F number | 3.91 |

-continued

Unit (in mm)

| Half-angle of view | 58.70555° |
|---|---|
| Image height | 0.886 |
| Entire length of lens | 7.1821 |

Embodiment 8

FIG. 15 is a sectional view along an optical axis showing the configuration of an objective lens for endoscope concerning Embodiment 8 of the present invention, FIGS. 16A, 12B, 16C, and 16D are graphic charts showing a spherical aberration, a coma aberration (meridional ray), a coma aberration (sagittal ray), and a distortion (astigmatism) in the optical system of Embodiment 8, respectively. The objective lens for endoscope of Embodiment 8 is composed of a front lens group G1, a rear lens group G2, and a brightness aperture stop S which is disposed between the front lens group G1 and the rear lens group G2. In FIG. 15, CG2 is a cover glass of CCD and IM is an image surface. Fundamental compositions of lenses of the front lens group G1 and the rear lens group G2 are nearly the same to those of Embodiment 1.

Next, numerical data of optical components which constitutes the objective lens for endoscope of Embodiment 8 will be shown.

Numerical Data of Embodiment 8

In the following surface data, S denotes aperture stop, and IM denotes image surface.

Unit (in mm)

Surface data

| Surface number | Radius of curvature | Surface interval | Refractive index | Abbe number |
|---|---|---|---|---|
| Object surface | ∞ | 15.5000 | | |
| 1 | ∞ | 0.4294 | 1.88815 | 40.76 |
| 2 | 0.7094 | 0.5505 | | |
| 3 | 2.6343 | 0.9601 | 1.93429 | 18.90 |
| 4 | 2.5635 | 0.1718 | | |
| 5 (S) | ∞ | 0.0515 | | |
| 6 | ∞ | 0.9164 | 1.88815 | 40.76 |
| 7 | −1.4589 | 0.1031 | | |
| 8 | 2.8190 | 0.9183 | 1.51825 | 64.14 |
| 9 | −1.7151 | 0.4638 | 1.93429 | 18.90 |
| 10 | −3.5655 | 1.4728 | | |
| 11 | ∞ | 1.2883 | 1.51825 | 64.14 |
| 12 | ∞ | 0 | | |
| 13 (IM) | ∞ | 0 | | |

Various data

| Focal length | 0.99999 |
|---|---|
| F number | 3.994 |
| Half-angle of view | 59.61560° |
| Image height | 0.891 |
| Entire length of lens | 7.3259 |

Embodiment 9

FIG. 17 is a sectional view along an optical axis showing the configuration of an objective lens for endoscope concerning Embodiment 9 of the present invention. FIGS. 18A, 18B, 18C, and 18D are graphic charts showing a spherical aberration, a coma aberration (meridional ray), a coma aberration (sagittal ray), and a distortion (astigmatism), respectively in the optical system of Embodiment 9. The objective lens for endoscope of Embodiment 9 is composed of a front lens group G1, a rear lens group G2, and a brightness aperture stop S which is disposed between the front lens group G1 and the rear lens group G2. In FIG. 17, CG is a cover glass, and IM is an image surface. The front lens group G1 is composed of, in order from an object side, a first lens L1 having a flat surface directed toward the object side, and a concave surface directed toward the image side; a second lens groups L2G; and it has negative refractive power as a whole. The second lens group L2G consist of a cemented lens in which in order from an object side, a lens L21 having positive refractive power, which has a meniscus form, and a convex surface directed toward the object side; and a lens L22 with negative refractive power which has a meniscus form, and a concave surface directed toward the image side are arranged and cemented. It has positive refractive power as a whole.

The fundamental composition of the rear lens group G2 is nearly the same that of Embodiment 1.

As mentioned above, the objective lens for an endoscope of Embodiment 9 is formed of a front lens group having a negative refractive power as a whole, a brightness aperture stop, and a rear lens group having positive refractive power as a whole. The front lens group consists of, in order from the object side, a first lens group formed of a single lens having negative refractive power, and a second lens group in which the lens surface of the second lens group closest to the image is concave, and. The second lens group has positive refractive power as a whole; and may be formed of a cemented lens. Since the second lens group may be formed as a cemented lens in the objective lens for an endoscope of Embodiment 9, aberration correction can be carried out more easily. In the objective lens for an endoscope of the present invention, the second lens group may be constituted with one lens, or it may be constituted with two or more lenses.

Next, numerical data of optical components which constitutes the objective lens for endoscope of Embodiment 9 will be shown.

Numerical Data of Embodiment 9

In the following surface data, S denotes Aperture stop, and IM denotes image surface.

| | Unit (in mm) | | | |
|---|---|---|---|---|
| | Surface data | | | |
| Surface number | Radius of curvature | Surface interval | Refractive index | Abbe number |
| Object surface | ∞ | 14.0000 | | |
| 1 | ∞ | 0.4731 | 1.88815 | 40.76 |
| 2 | 0.8690 | 0.6413 | | |
| 3 | 2.9919 | 0.6367 | 1.93429 | 18.90 |
| 4 | 7.5697 | 0.4731 | 1.67765 | 32.10 |
| 5 | 3.2171 | 0.0852 | | |
| 6 (S) | ∞ | 0.0568 | | |
| 7 | ∞ | 1.1186 | 1.88815 | 40.76 |
| 8 | −1.7300 | 0.1135 | | |
| 9 | 3.1016 | 1.0787 | 1.59143 | 61.14 |
| 10 | −1.6915 | 0.3804 | 1.93429 | 18.90 |
| 11 | −3.6123 | 1.0738 | | |

| | Unit (in mm) | | | |
|---|---|---|---|---|
| 11 | ∞ | 1.4193 | 1.51825 | 64.14 |
| 12 | ∞ | 0 | | |
| 13 (IM) | ∞ | 0 | | |

| Various data | |
|---|---|
| Focal length | 1.00000 |
| F number | 3.777 |
| Half-angle of view | 70.34747° |
| Image height | 0.982 |
| Entire length of lens | 7.5505 |

Embodiment 10

FIG. 19 is a sectional view showing the configuration of an objective lens for an endoscope along an optical axis concerning an Embodiment 10 according to the present invention. FIGS. 20A, 20B, 20C, and 20D are graphic charts showing a spherical aberration, a coma aberration (meridional ray), a coma aberration (sagittal ray), and a distortion (astigmatism), respectively in the optical system of Embodiment 10. The objective lens for the endoscope of Embodiment 10 is composed of a front lens group G1, a rear lens group G2, between which a brightness aperture stop S is inserted. In FIG. 19, CG is a cover glass, and IM is an image surface. Fundamental compositions of the front lens group G1, and the rear lens group G2 are nearly the same to those of Embodiment 1.

Here, in the objective lens for endoscope of Embodiment 10, as a glass material of the lens arranged closest to the object side in the front lens group G1, sapphire which has a low refractive index compared with those of materials used in other Embodiments is used. Embodiment 10 is an Embodiment of the first example of the present invention. In embodiments shown in Japanese Laid-Open Patent Application 2004-61763, Japanese Laid-Open Patent Application 2004-354888 and Japanese Laid-Open Patent Application Hei 8-122613, which are conventional examples of the present invention, refractive index of the glass material arranged at closest to the object side in the objective lens is 1.8 or more in all cases. This is because in the conventional examples, it is required that a strong negative power is given to the lens arranged at closest to the object side in the front lens group. Accordingly, when processability of a lens was taken into consideration, a glass material having high refractive index needed to be used. As this is generally known, if a lens having a certain form is replaced by a glass material having a low refractive index, it is equivalent to enlarging a curvature of the lens. Consequently, in conventional examples, if the first lens is constituted with a glass material having a low refractive index, a curvature of its concave surface becomes large, and accordingly it has been a problem in processing. For this reason, the glass material having high refractive index has been used.

In Embodiment 10, the composition of the example of the present invention is adopted. Namely, it is composed of, in order from an object side, a front lens group having negative refractive power as a whole; a brightness aperture stop; and a rear lens group having positive refractive power as a whole; wherein the front lens group is composed of, in order from an object side, a first lens group that may be formed of a single lens having negative refractive power; and a second lens group in which a lens surface closest to the image is concave, and the second lens group has positive refractive power as a whole. By such composition, a required negative refractive power of the front lens group is distributed from the first lens group to the second lens group while maintaining the power of the front lens group required as an objective lens for an endoscope. Accordingly, there is also a merit for removing restrictions on the refractive index of the lens in the first lens group having negative refractive power while keeping good processability of this lens. As mentioned above, according to the objective lens for an endoscope of Embodiment 10, as for the lens in the first lens group having negative refractive power, its ordinary optical glass can be easily replaced by glass material like sapphire having a larger Mohs hardness as compared with that of glass, namely, hard glass material.

Next, numerical data of optical components which constitutes the objective lens for endoscope of Embodiment 10 will be shown.

Numerical Data of Embodiment 10

In the following surface data, S denotes aperture stop, and IM denotes image surface.

| | Unit (in mm) | | | |
|---|---|---|---|---|
| | Surface data | | | |
| Surface number | Radius of curvature | Surface interval | Refractive index | Abbe number |
| Object surface | ∞ | 13.0000 | | |
| 1 | ∞ | 0.3200 | 1.77066 | 71.79 |
| 2 | 0.8204 | 0.5786 | | |
| 3 | 2.7305 | 1.1399 | 1.93429 | 18.90 |
| 4 | 2.6770 | 0.0777 | | |
| 5 (S) | ∞ | 0.0518 | | |
| 6 | ∞ | 0.9499 | 1.88815 | 40.76 |
| 7 | −1.4853 | 0.1036 | | |
| 8 | 2.9309 | 1.1053 | 1.59143 | 61.14 |
| 9 | −1.6874 | 0.4663 | 1.93429 | 18.90 |
| 10 | −3.3868 | 0.8635 | | |
| 11 | ∞ | 1.2780 | 1.51825 | 64.14 |
| 12 | ∞ | 0 | | |
| 13 (IM) | ∞ | 0 | | |

| Various data | |
|---|---|
| Focal length | 1.00000 |
| F number | 5.599 |
| Half-angle of view | 59.21840° |
| Image height | 0.896 |
| Entire length of lens | 6.9347 |

Embodiment 11

Figure 21:
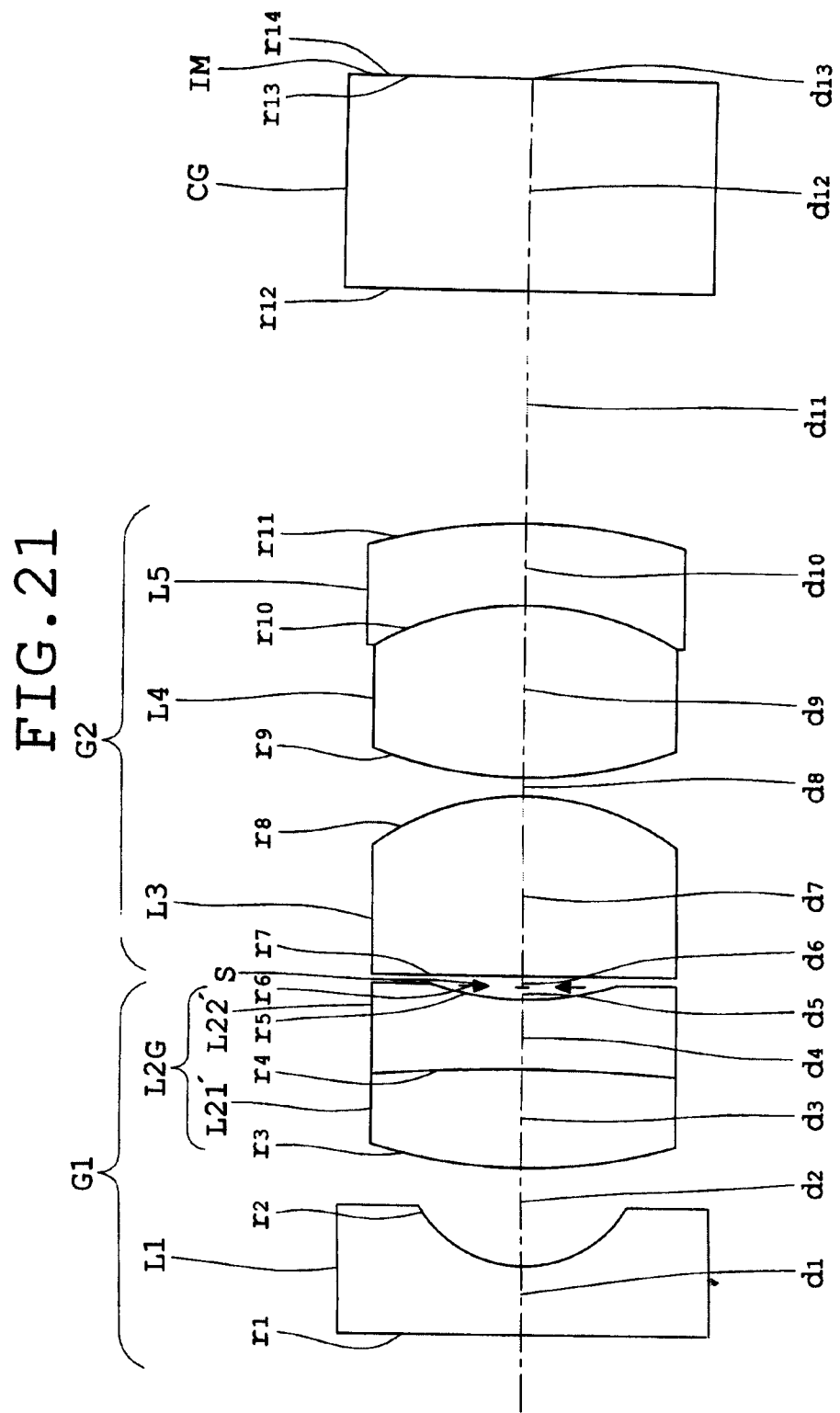
FIG. 21 is a sectional view showing the configuration of an objective lens for an endoscope according to Embodiment 11 of the present invention, the sectional view being taken along the optical axis.
Figure 22:
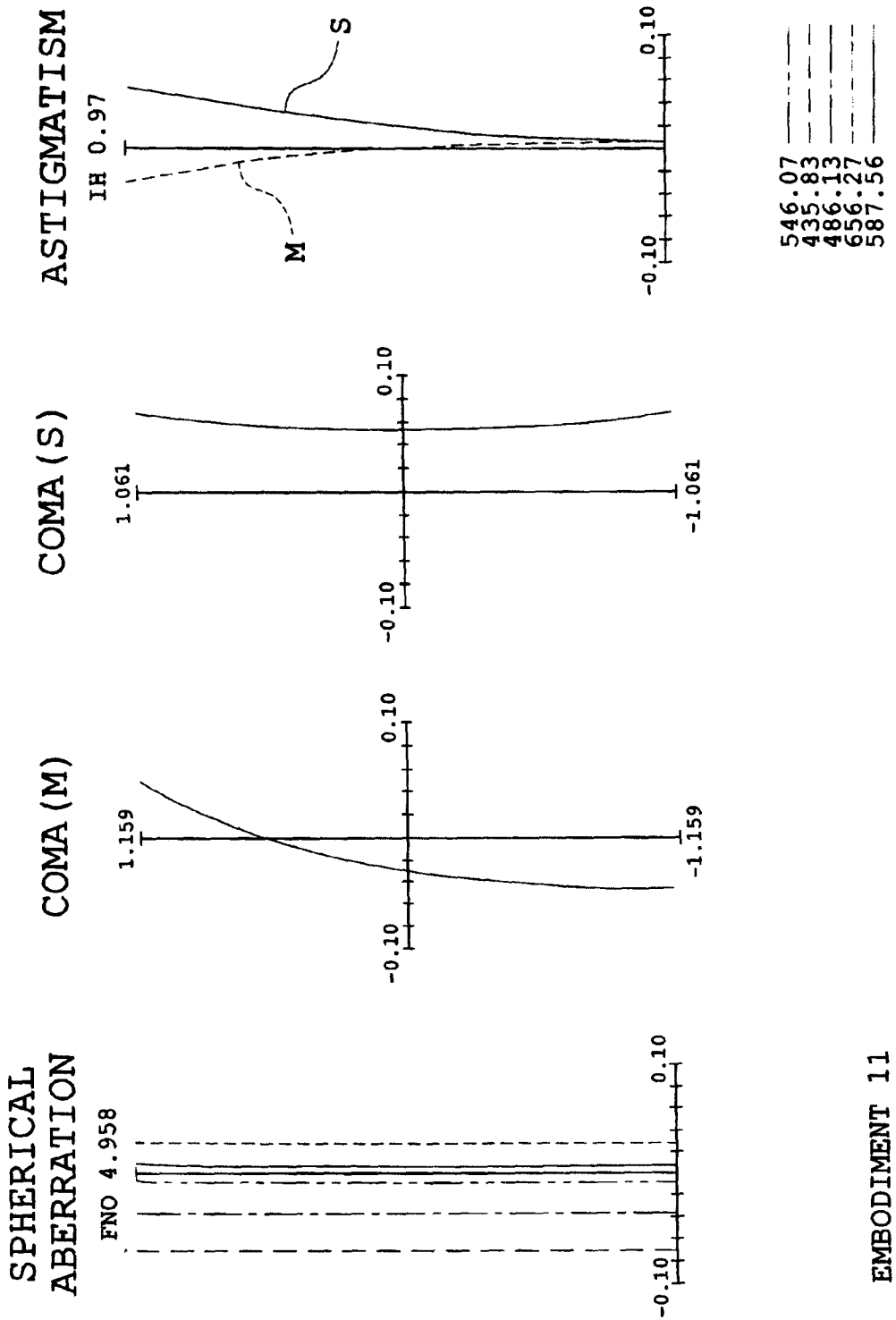
FIGS. 22A, 22B, 22C, and 22D are graphs showing spherical aberration, coma (meridional ray), coma (sagittal ray), and distortion (astigmatism) in an optical system according to Embodiment 11.

FIG. 21 is a sectional view showing the configuration of an objective lens for an endoscope along an optical axis concerning an Embodiment 11 according to the present invention. FIGS. 22A, 22B, 22C, and 22D are graphic charts showing a spherical aberration, a coma aberration (meridional ray), a coma aberration (sagittal ray), and a distortion (astigmatism) in the optical system of Embodiment 11, respectively. The objective lens for endoscope of Embodiment 11 is composed of a front lens group G1, a rear lens group G2, and a brightness aperture stop S which is disposed between the front lens group G1 and the rear lens group G2. In FIG. 21, CG is a cover glass of a CCD and IM is an image surface. The front lens group G1 is composed of, in order from an object side, a first lens group that is formed of a single lens L1 having a flat surface directed toward the object side, and a concave surface directed toward the image side; and a second lens groups L2G. The front lens group G1 has negative refractive power as a whole. The second lens group L2G is composed of, in order from the object side, a cemented lens in which a lens L21' having biconvex surfaces, and lens L22' having biconcave surfaces are arranged and cemented. The second lens group L2G has negative refractive power as a whole. The fundamental composition of the rear lens group G2 is nearly the same to that of Embodiment 1.

As mentioned above, according to the objective lens for an endoscope of Embodiment 11, it is composed of a front lens group having negative refractive power as a whole; a brightness aperture stop; and a rear lens group having positive refractive power as a whole. The front lens group has, in order from the object side, a first lens group that is formed of a single lens having negative refractive power; and a second lens group in which the lens surface closest to the image side is of concave form directed toward the image side. The second lens group has negative refractive power as a whole, and consists of a cemented lens. Since the second lens group is formed as a cemented lens in the objective lens for an endoscope of Embodiment 11, aberration correction can be carried out more easily. Furthermore, a shaping factor Q1 is calculated by the following:

$$Q1=(R_2+R_1)/(R_2-R_1)$$

where $R_1$ is the radius of curvature of a surface closest to the object side in the cemented lens, and $R_2$ is the radius of curvature of a surface closest to the image side in the cemented lens.

Next, numerical data of optical components which constitutes the objective lens for endoscope of Embodiment 11 will be shown.

Numerical Data of Embodiment 11

In the following surface data, S denotes aperture stop, and IM denotes image surface.

| | Unit (in mm) | | | |
|---|---|---|---|---|
| | Surface data | | | |
| Surface number | Radius of curvature | Surface interval | Refractive index | Abbe number |
| Object surface | ∞ | 17.0000 | | |
| 1 | ∞ | 0.4668 | 1.88815 | 40.76 |
| 2 | 0.8050 | 0.6629 | | |
| 3 | 3.7346 | 0.6536 | 1.93429 | 18.90 |
| 4 | −11.2039 | 0.4668 | 1.80922 | 39.59 |
| 5 | 2.2408 | 0.0861 | | |
| 6 (S) | ∞ | 0.0560 | | |
| 7 | ∞ | 1.1994 | 1.88815 | 40.76 |
| 8 | −1.6246 | 0.1027 | | |
| 9 | 2.7767 | 1.1401 | 1.51825 | 64.14 |
| 10 | −1.8905 | 0.5137 | 1.93429 | 18.90 |
| 11 | −3.6810 | 1.5200 | | |
| 11 | ∞ | 1.4005 | 1.51825 | 64.14 |
| 12 | ∞ | 0 | | |
| 13 (IM) | ∞ | 0 | | |

| Various data | |
|---|---|
| Focal length | 1.00000 |
| F number | 4.958 |
| Half angle of view | 69.06718° |
| Image height | 0.969 |
| Entire length of lens | 8.2686 |

Embodiment 12

Figure 23:
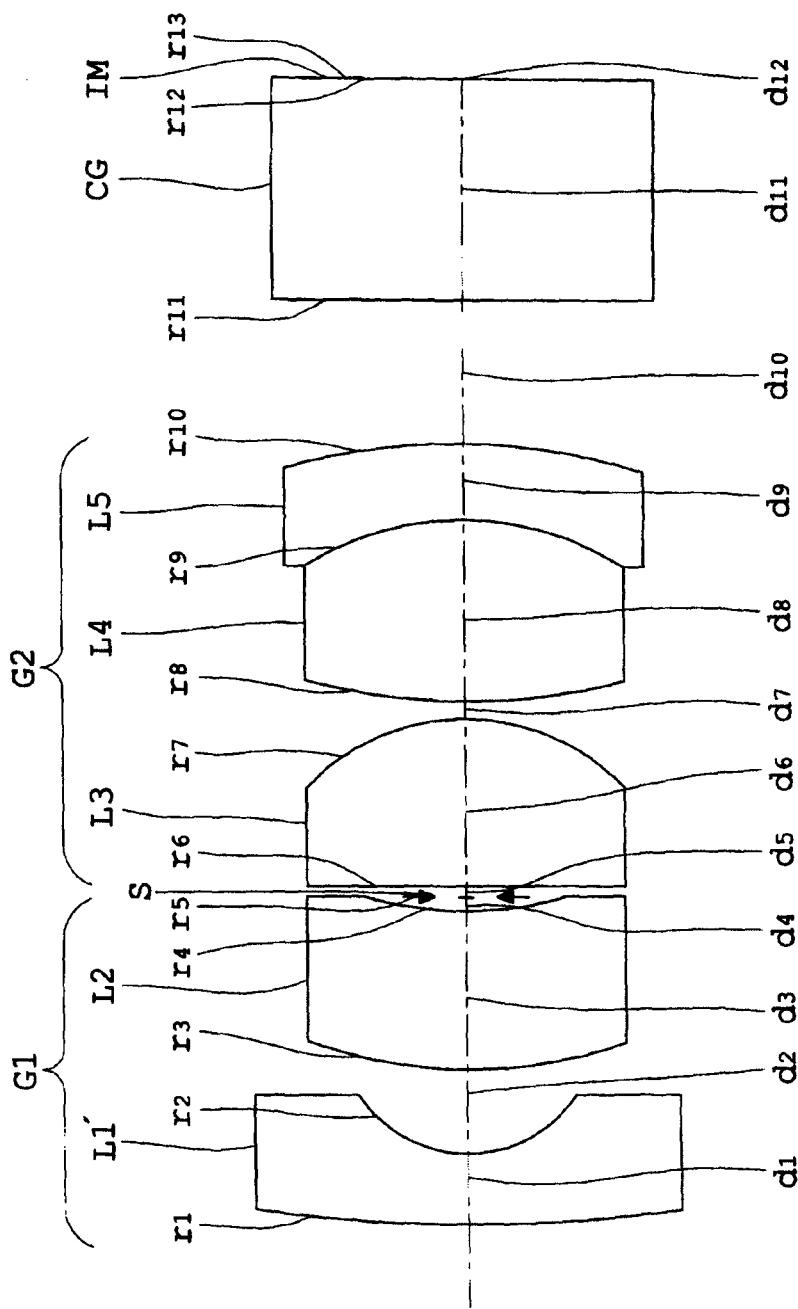
FIG. 23 is a sectional view showing the configuration of an objective lens for an endoscope according to Embodiment 12 of the present invention, the sectional view being taken along the optical axis.
Figure 24:
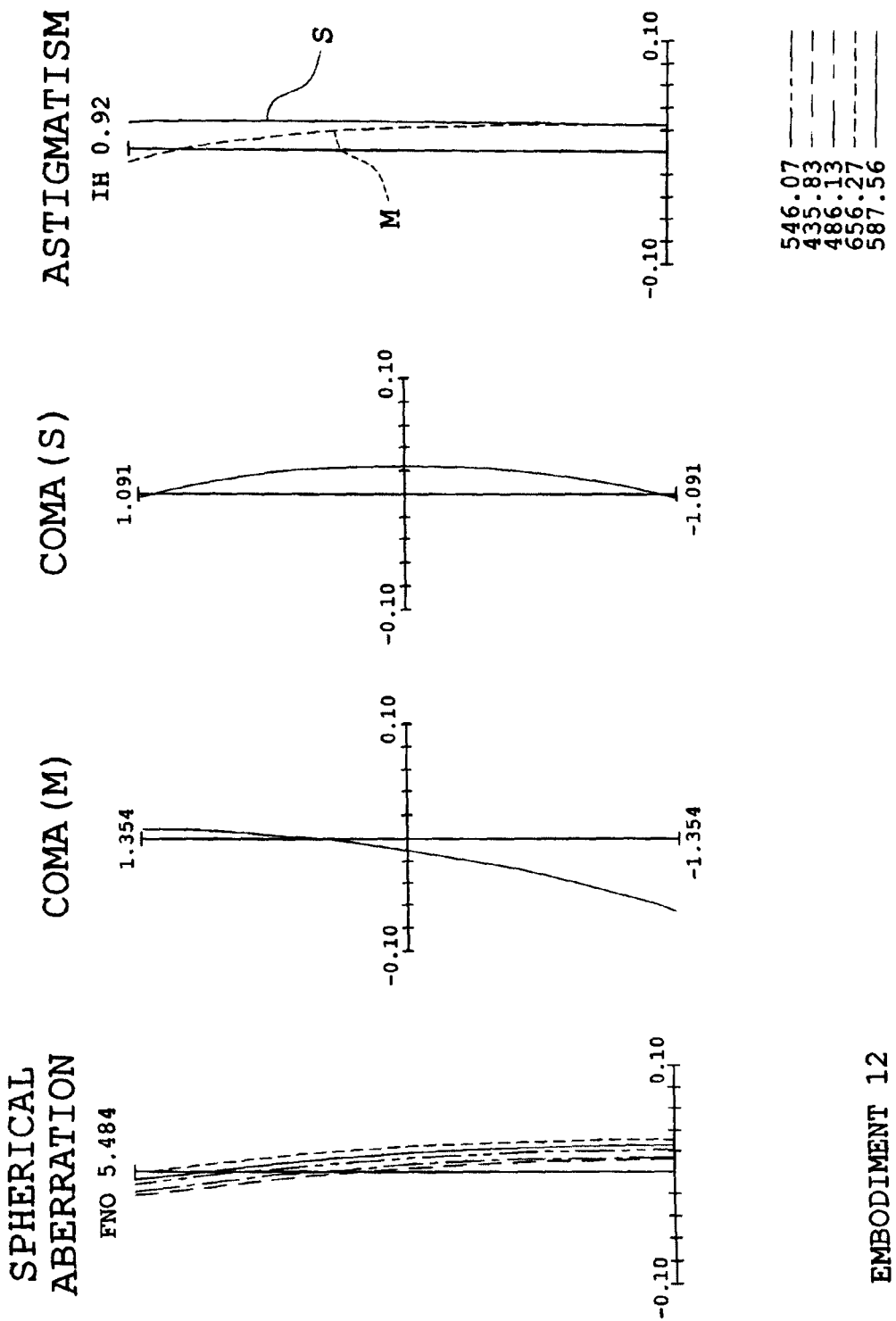
FIGS. 24A, 24B, 24C, and 24D are graphs showing spherical aberration, coma (meridional ray), coma (sagittal ray), and distortion (astigmatism) in an optical system according to Embodiment 12.

FIG. 23 is a sectional view showing the configuration of an objective lens for an endoscope along an optical axis concerning an Embodiment 12 according to the present invention. FIGS. 24A, 24B, 24C, and 24D are graphic charts showing a spherical aberration, a coma aberration (meridional ray), a coma aberration (sagittal ray), and a distortion (astigmatism) in the optical system of Embodiment 12, respectively. The objective lens for endoscope of Embodiment 12 is composed of a front lens group G1, a rear lens group G2, and a brightness aperture stop S which is disposed between the front lens group G1 and the rear lens group G2. In FIG. 23, CG is a cover glass and IM is an image surface. The front lens group G1 is composed of, in order from an object side, a first lens group that is formed of a single lens L1' of a meniscus form, which has negative refractive power, and a concave surface directed toward the image side; and a second lens group that is formed of a single lens L2 of meniscus form, has positive refractive power, and has its concave surface directed toward the image side. The front lens group G1 has negative refractive power as a whole. The fundamental composition of the rear lens group G2 is nearly the same to that of Embodiment 1.

Next, numerical data of optical components which constitutes the objective lens for endoscope of Embodiment 12 will be shown.

Numerical Data of Embodiment 12

In the following surface data, S denotes aperture stop, and IM denotes image surface.

| | Unit (in mm) | | | |
|---|---|---|---|---|
| | Surface data | | | |
| Surface number | Radius of curvature | Surface interval | Refractive index | Abbe number |
| Object surface | ∞ | 14.0000 | | |
| 1 | 8.8974 | 0.4449 | 1.88815 | 40.76 |
| 2 | 0.7919 | 0.5072 | | |
| 3 | 2.8134 | 0.9787 | 1.93429 | 18.90 |
| 4 | 2.4023 | 0.0801 | | |
| 5 (S) | ∞ | 0.0534 | | |
| 6 | ∞ | 0.9946 | 1.88815 | 40.76 |
| 7 | −1.2921 | 0.1068 | | |
| 8 | 3.2890 | 1.0947 | 1.59143 | 61.14 |
| 9 | −1.7180 | 0.4467 | 1.93429 | 18.90 |
| 10 | −3.6317 | 0.8542 | | |
| 11 | ∞ | 1.3346 | 1.51825 | 64.14 |
| 12 | ∞ | 0 | | |
| 13 (IM) | ∞ | 0 | | |

| Various data | |
|---|---|
| Focal length | 1.00000 |
| F number | 3.392 |
| Half-angle of view | 77.94567° |
| Image height | 0.932 |
| Entire length of lens | 8.0781 |

Embodiment 13

Figure 25:
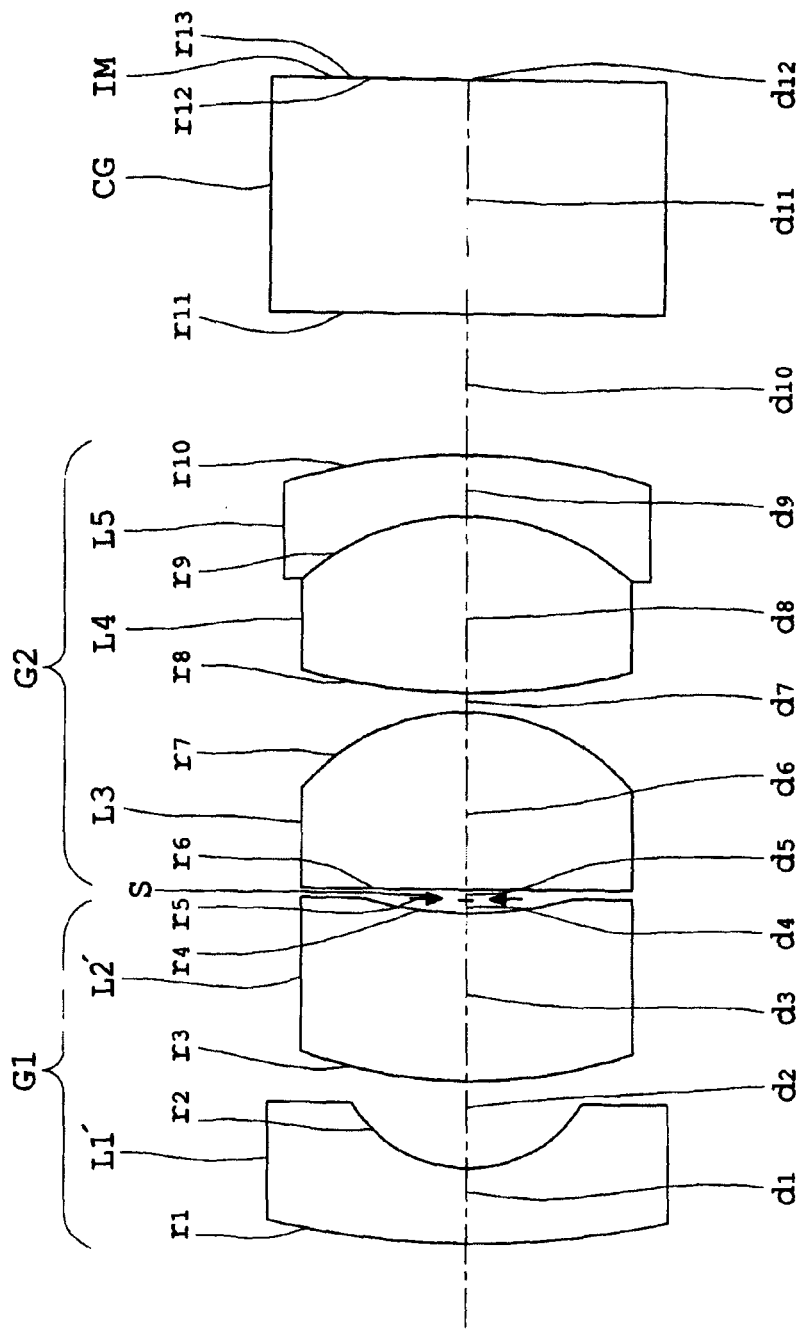
FIG. 25 is a sectional view showing the configuration of an objective lens for an endoscope according to Embodiment 13 of the present invention, the sectional view being taken along the optical axis.
Figure 26:
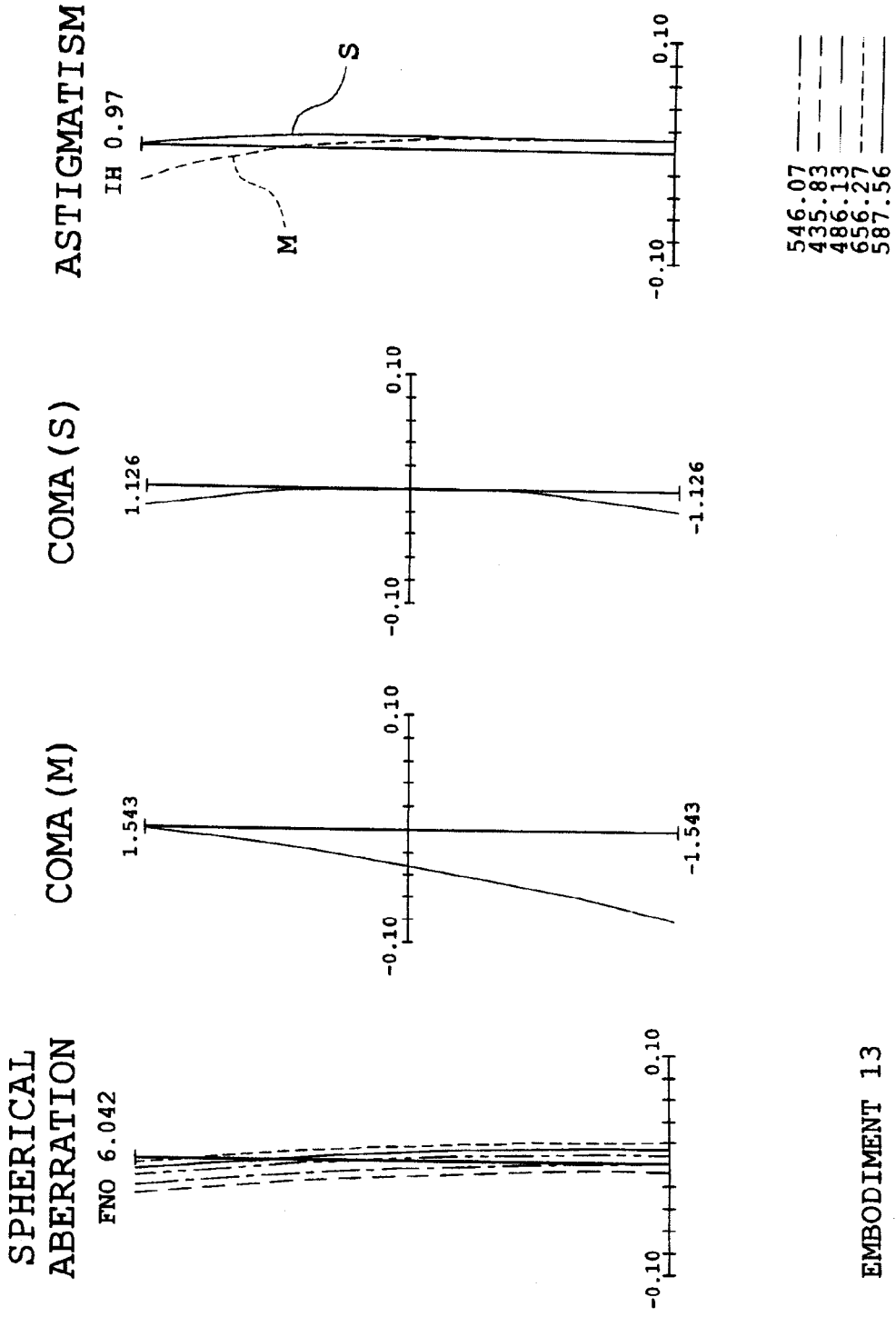
FIGS. 26A, 26B, 26C, and 26D are graphs showing spherical aberration, coma (meridional ray), coma (sagittal ray), and distortion (astigmatism) in an optical system according to Embodiment 13.

FIG. 25 is a sectional view along an optical axis showing the configuration of an objective lens for endoscope concerning Embodiment 13 of the present invention. FIGS. 26A, 24B, 24C, and 26D, are graphic charts showing a spherical aberration, a coma aberration (meridional ray), a coma aberration (sagittal ray), and a distortion (astigmatism) in the optical system of Embodiment 13, respectively. The objective lens for endoscope of Embodiment 13 is composed of a front lens group G1, a rear lens group G2, and a brightness aperture stop S which is disposed between the front lens group G1 and the rear lens group G2. In FIG. 25, CG is a cover glass and IM is an image surface. The front lens group G1 is composed of, in order from an object side, a first lens L1' of a meniscus form, which has negative refractive power, and a concave surface directed toward the image side; and a second lens L2' of a meniscus form, which has negative refractive power, and a concave surface directed toward the image side. The first lens L1' has negative refractive power as a whole. The fundamental composition of the rear lens group G2 is nearly the same to that of Embodiment 1.

Next, numerical data of optical components which constitute the objective lens for endoscope of Embodiment 13 will be shown.

Numerical Data of Embodiment 13

In the following surface data, S denotes aperture stop, and IM denotes image surface.

| | Unit (in mm) | | | |
|---|---|---|---|---|
| | Surface data | | | |
| Surface number | Radius of curvature | Surface interval | Refractive index | Abbe number |
| Object surface | ∞ | 13.0000 | | |
| 1 | 5.6171 | 0.4681 | 1.88815 | 40.76 |
| 2 | 0.8202 | 0.5336 | | |
| 3 | 3.3320 | 1.0298 | 1.93429 | 18.90 |
| 4 | 2.5277 | 0.0843 | | |
| 5 (S) | ∞ | 0.0562 | | |
| 6 | ∞ | 1.0531 | 1.88815 | 40.76 |
| 7 | −1.3336 | 0.1123 | | |
| 8 | 3.9736 | 1.0631 | 1.59143 | 61.14 |
| 9 | −1.4788 | 0.3722 | 1.85504 | 23.78 |
| 10 | −3.3480 | 0.8313 | | |
| 11 | ∞ | 1.4043 | 1.51825 | 64.14 |
| 12 | ∞ | 0 | | |
| 13 (IM) | ∞ | 0 | | |

| Various data | |
|---|---|
| Focal length | 1.00000 |
| F number | 6.042 |
| Half-angle of view | 59.69241° |
| Image height | 0.972 |
| Entire length of lens | 7.0084 |

Embodiment 14

Figure 27:
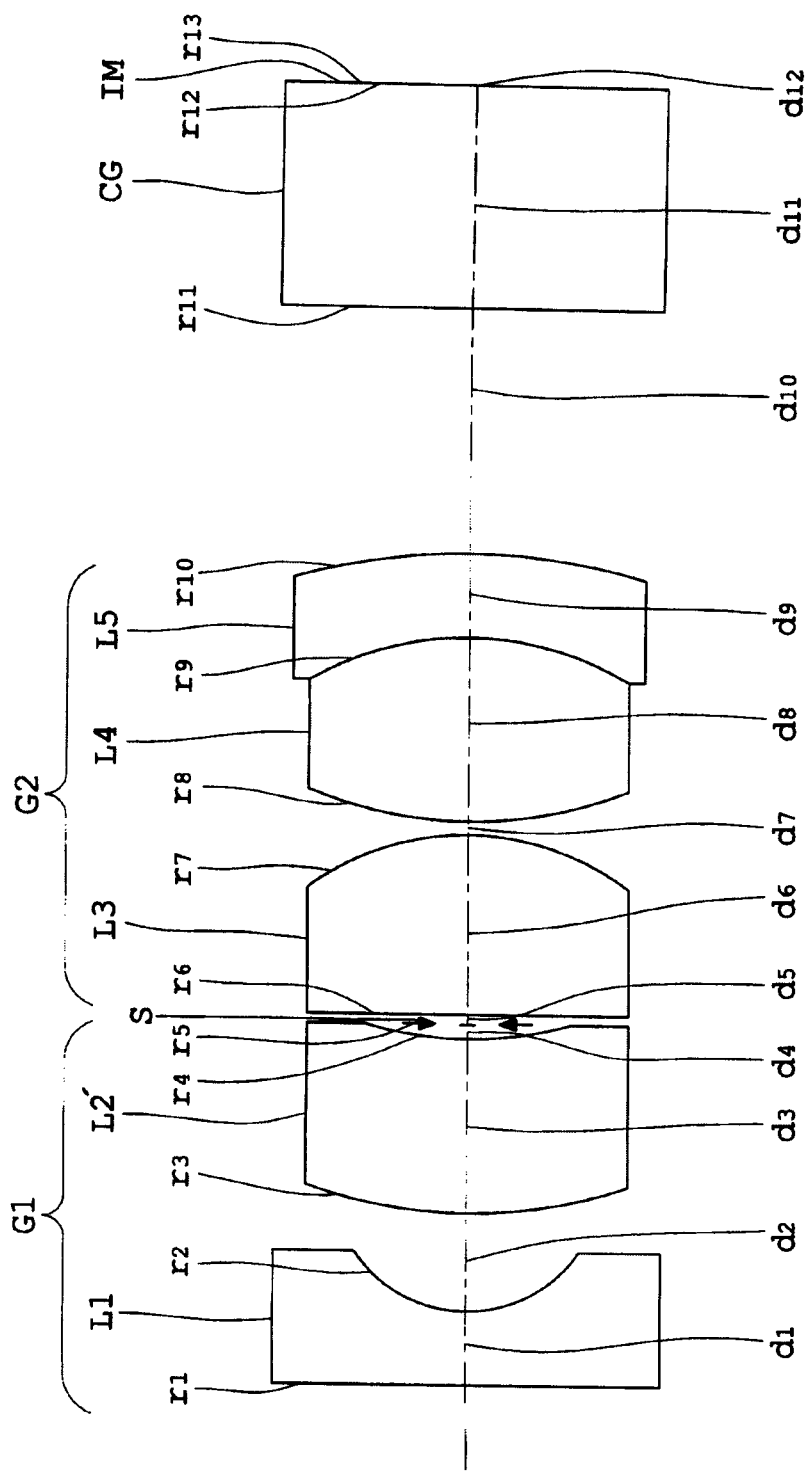
FIG. 27 is a sectional view showing the configuration of an objective lens for an endoscope according to Embodiment 14 of the present invention, the sectional view being taken along the optical axis.
Figure 28:
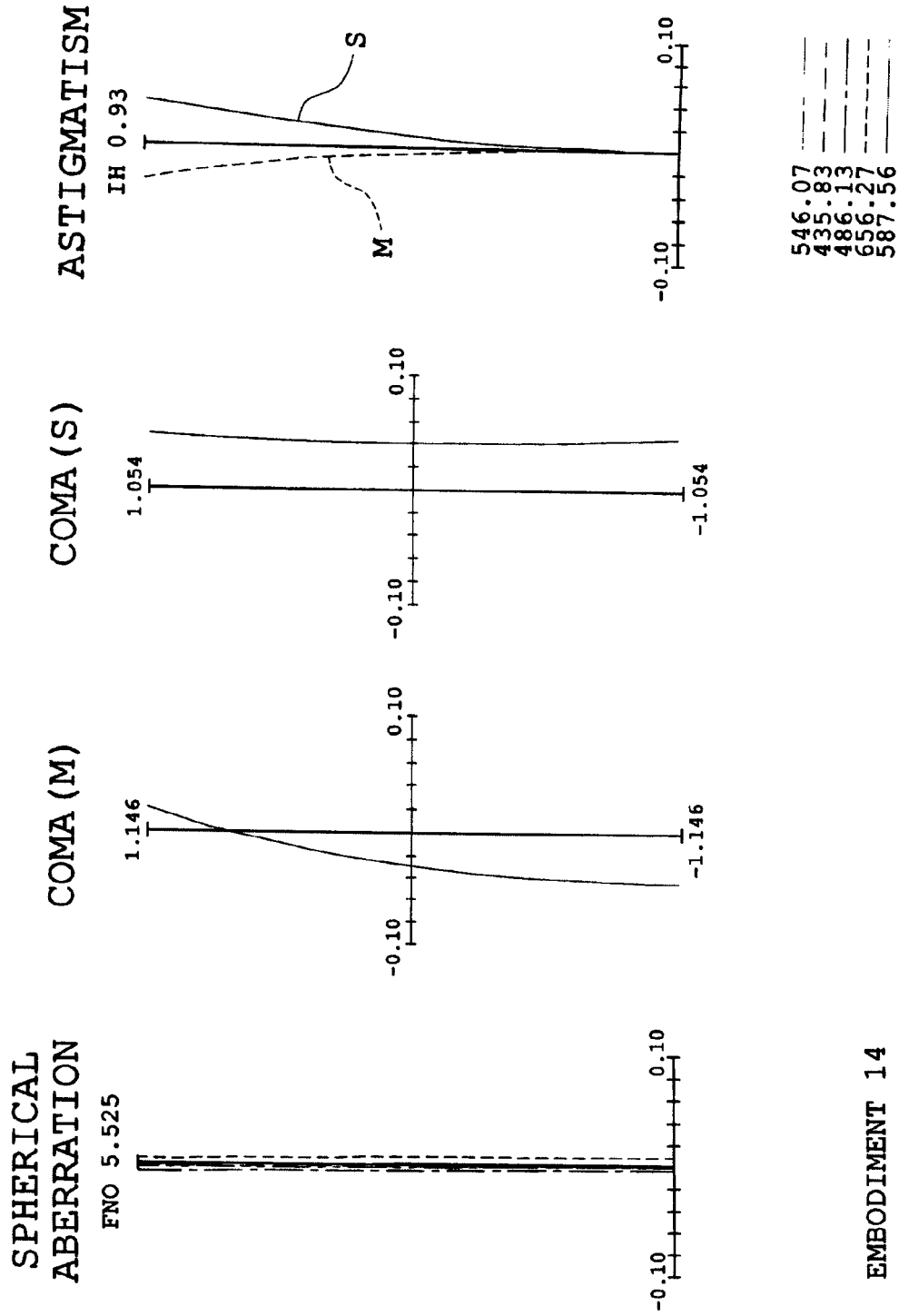
FIGS. 28A, 28B, 28C, and 28D are graphs showing spherical aberration, coma (meridional ray), coma (sagittal ray), and distortion (astigmatism) in an optical system according to Embodiment 14.

FIG. 27 is a sectional view along an optical axis showing the configuration of an objective lens for an endoscope concerning Embodiment 14 of the present invention. FIGS. 28A, 28B, 28C, and 28D, are graphic charts showing a spherical aberration, a coma aberration (meridional ray), a coma aberration (sagittal ray), and a distortion (astigmatism) in the optical system of Embodiment 14, respectively. The objective lens for an endoscope of Embodiment 14 is composed of a front lens group G1, a rear lens group G2, and a brightness aperture stop S which is disposed between the front lens group G1 and the rear lens group G2. In FIG. 27, CG is a cover glass and IM is an image surface. The front lens group G1 is composed of, in order from an object side, a first lens group that is formed of a single lens L1 of a plano-concave form, which has a flat surface directed toward an object side; and a second lens group that is formed of a single lens L2' of meniscus form, which has negative refractive power, and a concave surface directed toward the image side. The front lens group G1 has negative refractive power as a whole. The fundamental composition of the rear lens group G2 is nearly the same to that of Embodiment 1.

Next, numerical data of optical components which constitute the objective lens for endoscope of Embodiment 14 will be shown.

Numerical Data of Embodiment 14

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 16.0000 | | |
| 1 | ∞ | 0.4492 | 1.88815 | 40.76 |
| 2 | 0.7746 | 0.6379 | | |
| 3 | 2.9670 | 1.0475 | 1.93429 | 18.90 |
| 4 | 2.3355 | 0.0828 | | |
| 5 (S) | ∞ | 0.0539 | | |
| 6 | ∞ | 1.1140 | 1.88815 | 40.76 |
| 7 | −1.5434 | 0.0809 | | |
| 8 | 2.6719 | 1.0971 | 1.51825 | 64.14 |
| 9 | −1.8004 | 0.4943 | 1.93429 | 18.90 |
| 10 | −3.5420 | 1.4500 | | |
| 11 | ∞ | 1.3476 | 1.51825 | 64.14 |
| 12 | ∞ | 0 | | |
| 13 (IM) | ∞ | 0 | | |

| Various data | |
|---|---|
| Focal length | 1.00001 |
| F number | 5.525 |
| Half-angle of view | 64.22018° |
| Image height | 0.933 |
| Entire length of lens | 7.8551 |

Embodiment 15

Figure 29:
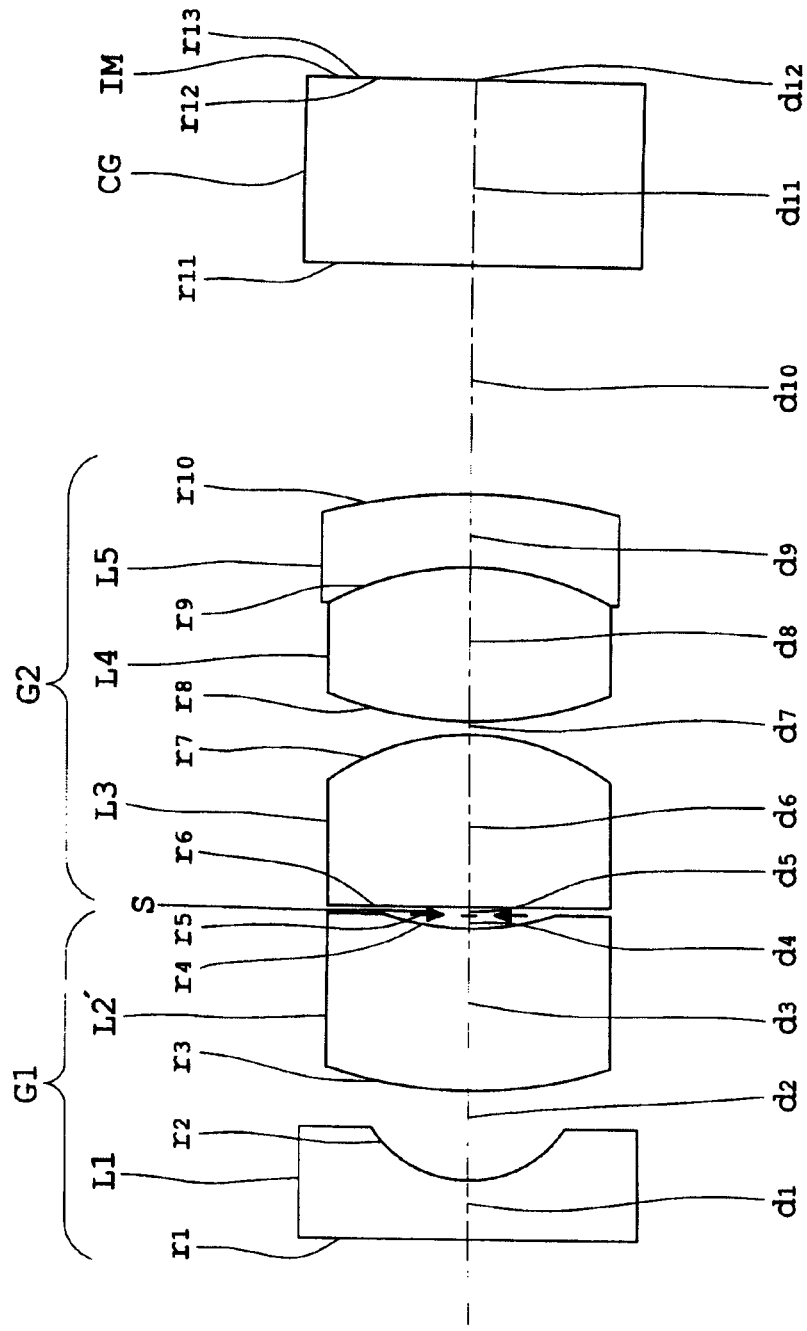
FIG. 29 is a sectional view showing the configuration of an objective lens for an endoscope according to Embodiment 15 of the present invention, the sectional view being taken along the optical axis.

FIG. 29 is a sectional view along an optical axis showing the configuration of an objective lens for endoscope concerning Embodiment 15 of the present invention. FIGS. 30A, 30B, 30C, and 30D are graphic charts showing a spherical aberration, a coma aberration (meridional ray), a coma aberration (sagittal ray), and a distortion (astigmatism) in the optical system of Embodiment 15, respectively. The objective lens for endoscope of Embodiment 15 is composed of, a front lens group G1, a rear lens group G2, and a brightness aperture stop S which is disposed between the front lens group G1 and the rear lens group G2. In FIG. 29, CG is a cover glass and IM is an image surface. Fundamental compositions of lenses of the front lens group G1 and the rear lens group G2 are nearly the same to those of Embodiment 14.

Next, numerical data of optical components which constitute the objective lens for endoscope of Embodiment 15 will be shown.

Numerical Data of Embodiment 15

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 16.0000 | | |
| 1 | ∞ | 0.4634 | 1.88815 | 40.76 |
| 2 | 0.8006 | 0.6593 | | |
| 3 | 3.1571 | 1.1980 | 1.93429 | 18.90 |
| 4 | 2.2285 | 0.0856 | | |
| 5 (S) | ∞ | 0.0557 | | |
| 6 | ∞ | 1.2443 | 1.88815 | 40.76 |
| 7 | −1.6101 | 0.0836 | | |
| 8 | 2.7616 | 1.1339 | 1.51825 | 64.14 |
| 9 | −1.8608 | 0.5109 | 1.93429 | 18.90 |
| 10 | −3.6609 | 1.6109 | | |
| 11 | ∞ | 1.3815 | 1.51825 | 64.14 |
| 12 | ∞ | 0 | | |
| 13 (IM) | ∞ | 0 | | |

| Various data | |
|---|---|
| Focal length | 0.99999 |
| F number | 6.636 |
| Half angle of view | 68.62833° |
| Image height | 0.964 |
| Entire length of lens | 8.4279 |

Embodiment 16

FIG. 31 is a sectional view along an optical axis showing the configuration of an objective lens for endoscope concerning Embodiment 16 of the present invention. FIGS. 32A, 32B, 32C, and 32D are graphic charts showing a spherical aberration, a coma aberration (meridional ray), a coma aberration (sagittal ray), and a distortion (astigmatism) in the optical system of Embodiment 16, respectively. The objective lens for endoscope of Embodiment 16 is composed of, a front lens group G1, a rear lens group G2, and a brightness aperture stop S which is disposed between the front lens group G1 and the rear lens group G2. In FIG. 31, CG is a cover glass and IM is an image surface. Fundamental compositions of lenses of the front lens group G1 and the rear lens group G2 are nearly the same to those of Embodiment 14.

Next, numerical data of optical components which constitute the objective lens for endoscope of Embodiment 16 will be shown.

Numerical Data of Embodiment 16

In the following surface data, S denotes aperture stop, and IM denotes image surface.

| Unit (in mm) | | | | |
|---|---|---|---|---|
| Surface data | | | | |
| Surface number | Radius of curvature | Surface interval | Refractive index | Abbe number |
| Object surface | ∞ | 16.5000 | | |
| 1 | ∞ | 0.4634 | 1.88815 | 40.76 |
| 2 | 0.7991 | 0.6210 | | |
| 3 | 3.1514 | 1.1122 | 1.93429 | 18.90 |
| 4 | 2.0391 | 0.0855 | | |
| 5 (S) | ∞ | 0.0556 | | |
| 6 | ∞ | 1.2420 | 1.88815 | 40.76 |

-continued

| | | Unit (in mm) | | |
|---|---|---|---|---|
| 7 | −1.5479 | 0.0834 | | |
| 8 | 2.7566 | 1.1318 | 1.51825 | 64.14 |
| 9 | −1.8574 | 0.5100 | 1.93429 | 18.90 |
| 10 | −3.6543 | 1.1122 | | |
| 11 | ∞ | 2.1318 | 1.51825 | 64.14 |
| 12 | ∞ | 0 | | |
| 13 (IM) | ∞ | 0 | | |

Various data

| Focal length | 1.00000 |
|---|---|
| F number | 6.47 |
| Half angle of view | 63.68250° |
| Image height | 0.927 |
| Entire length of lens | 8.5490 |

Embodiment 17

Figure 33:
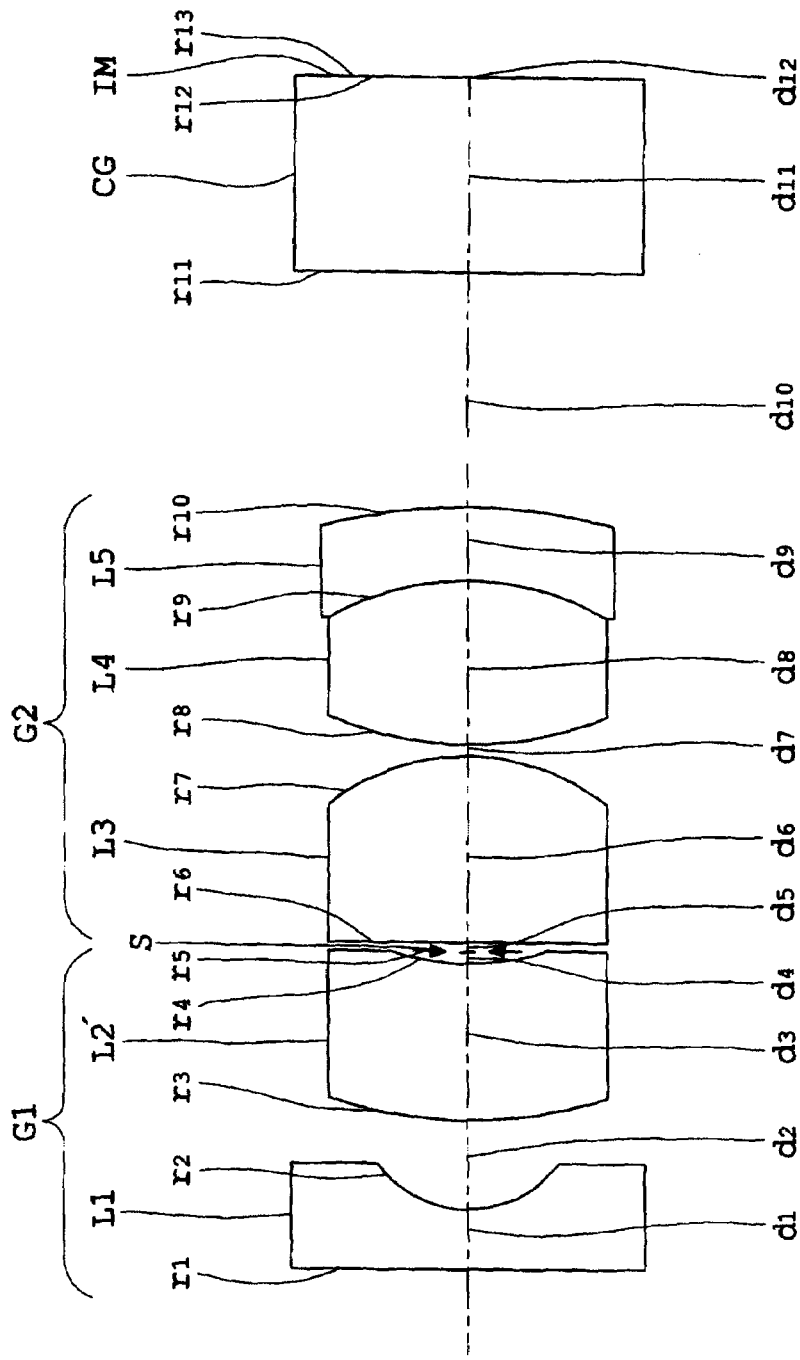
FIG. 33 is a sectional view showing the configuration of an objective lens for an endoscope according to Embodiment 17 of the present invention, the sectional view being taken along the optical axis.

FIG. 33 is a sectional view along an optical axis showing the configuration of an objective lens for endoscope concerning Embodiment 17 of the present invention. FIGS. 34A, 34B, 34C, and 34D, are graphic charts showing a spherical aberration, a coma aberration (meridional ray), a coma aberration (sagittal ray), and a distortion (astigmatism) in the optical system of Embodiment 17, respectively. The objective lens for endoscope of Embodiment 17 is composed of a front lens group G1, a rear lens group G2, and a brightness aperture stop S which is disposed between the front lens group G1 and the rear lens group G2. In FIG. 33, CG is a cover glass and IM is an image surface. Fundamental compositions of lenses of the front lens group G1 and the rear lens group G2 are nearly the same to those of Embodiment 14.

Next, numerical data of optical components which constitutes the objective lens for endoscope of Embodiment 17 will be shown.

Numerical Data of Embodiment 17

In the following surface data, S denotes aperture stop, and IM denotes image surface.

Unit (in mm)

Surface data

| Surface number | Radius of curvature | Surface interval | Refractive index | Abbe number |
|---|---|---|---|---|
| Object surface | ∞ | 17.0000 | | |
| 1 | ∞ | 0.4809 | 1.88815 | 40.76 |
| 2 | 0.8293 | 0.6444 | | |
| 3 | 3.2702 | 1.1542 | 1.93429 | 18.90 |
| 4 | 1.9236 | 0.0887 | | |
| 5 (S) | ∞ | 0.0577 | | |
| 6 | ∞ | 1.3465 | 1.88815 | 40.76 |
| 7 | −1.5774 | 0.0866 | | |
| 8 | 2.8605 | 1.1745 | 1.51825 | 64.14 |
| 9 | −1.9275 | 0.5292 | 1.93429 | 18.90 |
| 10 | −3.7921 | 1.6686 | | |
| 11 | ∞ | 1.4235 | 1.51825 | 64.14 |
| 12 | ∞ | 0 | | |
| 13 (IM) | ∞ | 0 | | |

Various data

| Focal length | 1.00000 |
|---|---|
| F number | 7.345 |

Unit (in mm)

| Half angle of view | 66.72419° |
|---|---|
| Image height | 0.950 |
| Entire length of lens | 8.6547 |

Next, values of the conditional parameter in each Embodiment will be shown in Table 1.

TABLE 1

| | Condition (1) $\lvert f_0/f_1 \rvert \leq 1.1$ | Condition (2) $\lvert f_0/f \rvert$ | $\lvert f_1/f \rvert$ | Condition (2) $-10 \leq Q1 \leq -2$ | Condition (3) $\lvert f_0/f_1 \rvert < 0.81$ |
|---|---|---|---|---|---|
| Embodiment 1 | 1.088 | 1.03 | 0.947 | — | — |
| Embodiment 2 | 0.927 | 0.928 | 1 | — | — |
| Embodiment 3 | 0.89 | 0.845 | 0.95 | — | — |
| Embodiment 4 | 0.85 | 0.838 | 0.986 | — | — |
| Embodiment 5 | 0.832 | 0.83 | 0.996 | — | — |
| Embodiment 6 | 0.974 | 0.917 | 0.942 | — | — |
| Embodiment 7 | 0.911 | 0.731 | 0.802 | — | — |
| Embodiment 8 | 0.903 | 0.721 | 0.799 | — | — |
| Embodiment 9 | 1.038 | 1.016 | 0.978 | — | — |
| Embodiment 10 | 0.908 | 0.967 | 1.065 | — | — |
| Embodiment 11 | — | 0.706 | 0.906 | −4 | 0.779 |
| Embodiment 12 | 0.845 | 0.848 | 1.005 | — | — |
| Embodiment 13 | — | 0.905 | 1.133 | −7.285 | 0.799 |
| Embodiment 14 | — | 0.702 | 0.872 | −8.396 | 0.805 |
| Embodiment 15 | — | 0.677 | 0.901 | −5.8 | 0.751 |
| Embodiment 16 | — | 0.647 | 0.9 | −4.667 | 0.719 |
| Embodiment 17 | — | 0.633 | 0.934 | −3.857 | 0.678 |

As is apparent from the right-most column of Table 1, the present invention also satisfies the following Condition (3') that is more narrow than the previously discussed Condition (3):

$$0.678 \leq \lvert f_0/f_1 \rvert < 0.81 \quad (3').$$

As comparative examples of the present invention, values corresponding to the conditional parameters of the present invention of Japanese Laid-Open Patent Application 2004-61763, Japanese Laid-Open Patent Application 2004-354888, Japanese Laid-Open Patent Application Hei 8-122632, and Japanese Laid-Open Patent Application Hei 10-20189 will be shown in the following table 2. Embodiments and comparative examples in Table 2 are Embodiments and comparative examples shown in Japanese Laid-Open Patent Application 2004-61763, Japanese Laid-Open Patent Application 2004-354888, Japanese Laid-Open Patent Application Hei 8-122632, and Japanese Laid-Open Patent Application Hei 10-20189.

TABLE 2

| | condition (1) $\lvert f_0/f_1 \rvert \leq 1.1$ | $\lvert f_0/f \rvert$ | $\lvert f_1/f \rvert$ | condition (2) $-10 \leq Q1 \leq -2$ | condition (3) $\lvert f_0/f_1 \rvert < 0.81$ |
|---|---|---|---|---|---|
| 2004-61763 | | | | | |
| comparative example 1 | 3.002 | 1.917 | 0.637 | — | — |
| comparative example 2 | 1.455 | 0.79 | 0.543 | — | — |
| Embodiment 1 | 1.175 | 0.918 | 0.781 | — | — |
| Embodiment 2 | 1.127 | 1.032 | 0.915 | — | — |

TABLE 2-continued

|  | condition (1) $|f_0/f_1| \leq 1.1$ | $|f_0/f|$ | $|f_1/f|$ | condition (2) $-10 \leq Q1 \leq -2$ | condition (3) $|f_0/f_1| < 0.81$ |
|---|---|---|---|---|---|
| 2004-354888 |  |  |  |  |  |
| Embodiment 1 | 1.609 | 1.471 | 0.914 | — | — |
| Embodiment 2 | 1.455 | 1.381 | 0.95 | — | — |
| Embodiment 3 | 1.757 | 1.729 | 0.984 | — | — |
| Embodiment 4 | 1.469 | 1.505 | 1.024 | — | — |
| Embodiment 5 | 1.945 | 1.804 | 0.927 | — | — |
| Embodiment 6 | 1.568 | 1.428 | 0.911 | — | — |
| Embodiment 7 | 1.411 | 1.34 | 0.95 | — | — |
| Embodiment 8 | 1.449 | 1.314 | 0.907 | — | — |
| Embodiment 9 | 1.267 | 1.168 | 0.923 | — | — |
| Embodiment 10 | 1.395 | 1.169 | 0.838 | — | — |
| Embodiment 11 | 1.198 | 1.173 | 0.979 | — | — |
| Hei 8-122632 |  |  |  |  |  |
| Embodiment 1 | 1.459 | 0.788 | 0.54 | — | — |
| Embodiment 2 | 1.482 | 0.999 | 0.674 | — | — |
| Embodiment 3 | 2.163 | 1.497 | 0.692 | — | — |
| Hei 10-20189 |  |  |  |  |  |
| Embodiment 1 | — | 1.283 | 4.78 | 2.88 | 0.268 |
| Embodiment 2 | — | 1.392 | 1.936 | 5.54 | 0.719 |
| Embodiment 3 | — | 0.544 | 0.582 | 7.00 | 0.933 |
| Embodiment 4 | — | 1.013 | 1.516 | 2.38 | 0.668 |
| Embodiment 5 | — | 1.164 | 2.791 | 0.25 | 0.417 |
| Embodiment 6 | — | 1.668 | 2.471 | −0.09 | 0.675 |
| Embodiment 7 | — | 1.183 | 1.673 | 1.44 | 0.707 |
| Embodiment 8 | — | 1.705 | 2.574 | 1.00 | 0.663 |
| Embodiment 9 | — | 1.302 | 2.29 | 1.00 | 0.568 |
| Embodiment 10 | — | 1.63 | 2.186 | 1.00 | 0.747 |

The objective lens for endoscope according to the present invention is useful in the field of medical treatment or industry where observation of a thin pore having small diameter such as a narrow vessel or space in a patient's body etc., by using an endoscope is required.

What is claimed is:

1. An objective lens for an endoscope comprising, in order from an object side:
    a front lens group having negative refractive power as a whole;
    a brightness aperture stop; and
    a rear lens group having positive refractive power as a whole;
    wherein
        said front lens group comprises, in order from the object side,
        a first lens group having negative refractive power that may include only a single lens; and
        a second lens group that may include only a single lens, said second lens group having a lens surface closest to the image side that is of a concave form directed toward the image side, said second lens group having positive refractive power as a whole; and the following condition (1) is satisfied:

$$|f_0/f_1| < 1.1 \qquad (1)$$

where
        $f_0$ is the composite focal length of said front lens group, and
        $f_1$ is the focal length of said first lens group; and
    wherein there is an air space between said first lens group and said second lens group.

2. The objective lens for an endoscope according to claim 1, wherein said rear lens group comprises, in order from the object side: a positive lens, and a cemented lens formed of a positive lens joined to a negative lens.

3. An objective lens for an endoscope comprising, in order from an object side:
    a front lens group having negative refractive power as a whole;
    a brightness aperture stop; and
    a rear lens group having positive refractive power as a whole;
    wherein
        said front lens group comprises, in order from the object side,
        a first lens group having negative refractive power that may include only a single lens; and
        a second lens group having positive refractive power as a whole that may include only a single lens;
    and the following condition (1) is satisfied:

$$|f_0/f_1| < 1.1 \qquad (1)$$

where
        $f_0$ is the composite focal length of said front lens group, and
        $f_1$ is the focal length of said first lens group; and
    wherein there is an air space between said first lens group and said second lens group.

4. The objective lens for an endoscope according to claim 3, wherein said rear lens group comprises, in order from the object side: a positive lens, and a cemented lens formed of a positive lens joined to a negative lens.

* * * * *